United States Patent
Kim et al.

(10) Patent No.: US 8,145,301 B2
(45) Date of Patent: *Mar. 27, 2012

(54) BLENDING CARDIAC RHYTHM DETECTION PROCESSES

(75) Inventors: Jaeho Kim, Redmond, WA (US); Joseph M. Bocek, Seattle, WA (US); Julie A. Thompson, Circle Pines, MN (US); Eric G. Lovett, Mendota Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/895,151

(22) Filed: Sep. 30, 2010

(65) Prior Publication Data

US 2011/0021934 A1   Jan. 27, 2011

Related U.S. Application Data

(63) Continuation of application No. 11/089,185, filed on Mar. 24, 2005, now Pat. No. 7,818,056.

(51) Int. Cl.
*A61N 1/39* (2006.01)
*A61N 1/362* (2006.01)

(52) U.S. Cl. ............... 607/5; 600/510; 607/14
(58) Field of Classification Search ...... 607/5; 600/515, 600/518, 508

See application file for complete search history.

(56) References Cited

U.S. PATENT DOCUMENTS

| | | |
|---|---|---|
| 4,023,564 A | 5/1977 | Valiquette et al. |
| 4,336,810 A | 6/1982 | Anderson et al. |
| 4,428,378 A | 1/1984 | Anderson et al. |
| 4,550,221 A | 10/1985 | Mabusth |
| 4,686,332 A | 8/1987 | Greanias et al. |
| 4,830,006 A | 5/1989 | Haluska et al. |
| 4,865,036 A | 9/1989 | Chirife |
| 4,872,459 A | 10/1989 | Pless et al. |
| 4,880,005 A | 11/1989 | Pless et al. |
| 5,002,052 A | 3/1991 | Haluska |
| 5,107,850 A | 4/1992 | Olive |
| 5,144,947 A | 9/1992 | Wilson |
| 5,158,092 A | 10/1992 | Glace |
| 5,161,527 A | 11/1992 | Nappholz et al. |
| 5,161,529 A | 11/1992 | Stotts et al. |

(Continued)

FOREIGN PATENT DOCUMENTS

EP   0360412 A1   3/1990

(Continued)

OTHER PUBLICATIONS

"U.S. Appl. No. 11/089,185, Advisory Action mailed Feb. 25, 2009", 3 pgs.

(Continued)

*Primary Examiner* — Carl H. Layno
*Assistant Examiner* — Jon-Eric C. Morales
(74) *Attorney, Agent, or Firm* — Schwegman, Lundberg & Woessner, P.A.

(57) ABSTRACT

Systems and methods are described for classifying a cardiac rhythm. A cardiac rhythm is classified using a classification process that includes a plurality of cardiac rhythm discriminators. Each rhythm discriminator provides an independent classification of the cardiac rhythm. The classification process is modified if the modification is likely to produce enhanced classification results. The rhythm is reclassified using the modified classification process.

23 Claims, 15 Drawing Sheets

U.S. PATENT DOCUMENTS

| | | | |
|---|---|---|---|
| 5,176,137 A | 1/1993 | Erickson et al. | |
| 5,181,511 A | 1/1993 | Nickolls et al. | |
| 5,193,550 A | 3/1993 | Duffin | |
| 5,209,229 A | 5/1993 | Gilli | |
| 5,217,021 A | 6/1993 | Steinhaus et al. | |
| 5,222,493 A | 6/1993 | Sholder | |
| 5,224,475 A | 7/1993 | Berg et al. | |
| 5,251,624 A | 10/1993 | Bocek et al. | |
| 5,257,621 A | 11/1993 | Bardy et al. | |
| 5,312,441 A | 5/1994 | Mader et al. | |
| 5,312,445 A | 5/1994 | Nappholz et al. | |
| 5,324,310 A | 6/1994 | Greeninger et al. | |
| 5,327,900 A | 7/1994 | Mason et al. | |
| 5,330,505 A | 7/1994 | Cohen | |
| 5,330,508 A | 7/1994 | Gunderson | |
| 5,342,402 A | 8/1994 | Olson et al. | |
| 5,350,410 A | 9/1994 | Kleks et al. | |
| 5,379,776 A | 1/1995 | Murphy et al. | |
| 5,411,031 A | 5/1995 | Yomtov | |
| 5,411,530 A | 5/1995 | Akhtar | |
| 5,425,749 A | 6/1995 | Adams | |
| 5,447,519 A | 9/1995 | Peterson | |
| 5,458,620 A | 10/1995 | Adams et al. | |
| 5,462,060 A | 10/1995 | Jacobson et al. | |
| 5,472,453 A | 12/1995 | Alt | |
| 5,513,644 A | 5/1996 | McClure et al. | |
| 5,548,619 A | 8/1996 | Horiike et al. | |
| 5,554,177 A | 9/1996 | Kieval et al. | |
| 5,587,970 A | 12/1996 | Greenwood | |
| 5,587,977 A | 12/1996 | Murata | |
| 5,662,688 A | 9/1997 | Haefner et al. | |
| 5,683,424 A | 11/1997 | Brown et al. | |
| 5,683,431 A | 11/1997 | Wang | |
| 5,685,315 A | 11/1997 | McClure et al. | |
| 5,725,559 A | 3/1998 | Alt et al. | |
| 5,755,737 A | 5/1998 | Prieve et al. | |
| 5,779,645 A | 7/1998 | Olson et al. | |
| 5,782,888 A | 7/1998 | Sun et al. | |
| 5,817,027 A | 10/1998 | Arand et al. | |
| 5,836,971 A | 11/1998 | Starkweather | |
| 5,844,506 A | 12/1998 | Binstead | |
| 5,846,263 A | 12/1998 | Peterson et al. | |
| 5,855,593 A | 1/1999 | Olson et al. | |
| 5,857,977 A | 1/1999 | Caswell et al. | |
| 5,871,512 A | 2/1999 | Hemming et al. | |
| 5,891,170 A | 4/1999 | Nitzsche et al. | |
| 5,893,882 A | 4/1999 | Peterson et al. | |
| 5,978,707 A | 11/1999 | Krig et al. | |
| 5,999,854 A | 12/1999 | Deno et al. | |
| 6,064,906 A | 5/2000 | Langberg et al. | |
| 6,076,014 A | 6/2000 | Alt | |
| 6,084,953 A | 7/2000 | Johnson et al. | |
| 6,101,414 A | 8/2000 | Kroll | |
| 6,128,529 A | 10/2000 | Elser | |
| 6,137,308 A | 10/2000 | Nayak | |
| 6,147,680 A | 11/2000 | Tareev | |
| 6,151,524 A | 11/2000 | Krig et al. | |
| 6,167,308 A | 12/2000 | DeGroot | |
| 6,178,350 B1 | 1/2001 | Olson et al. | |
| 6,185,459 B1 | 2/2001 | Mehra et al. | |
| 6,192,273 B1 | 2/2001 | Igel et al. | |
| 6,192,275 B1 | 2/2001 | Zhu et al. | |
| 6,212,428 B1 | 4/2001 | Hsu et al. | |
| 6,221,011 B1 | 4/2001 | Bardy | |
| 6,223,078 B1 | 4/2001 | Marcovecchio | |
| 6,230,055 B1 | 5/2001 | Sun et al. | |
| 6,253,102 B1 | 6/2001 | Hsu et al. | |
| 6,266,554 B1 | 7/2001 | Hsu et al. | |
| 6,270,457 B1 | 8/2001 | Bardy | |
| 6,275,732 B1 | 8/2001 | Hsu et al. | |
| 6,277,072 B1 | 8/2001 | Bardy | |
| 6,280,380 B1 | 8/2001 | Bardy | |
| 6,289,248 B1 | 9/2001 | Conley et al. | |
| 6,308,095 B1 | 10/2001 | Hsu et al. | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,393,316 B1 | 5/2002 | Gillberg et al. | |
| 6,398,728 B1 | 6/2002 | Bardy | |
| 6,400,986 B1 | 6/2002 | Sun et al. | |
| 6,418,340 B1 | 7/2002 | Conley et al. | |
| 6,434,417 B1 | 8/2002 | Lovett | |
| 6,438,407 B1 | 8/2002 | Ousdigian et al. | |
| 6,438,410 B2 | 8/2002 | Hsu et al. | |
| 6,440,066 B1 | 8/2002 | Bardy | |
| 6,445,949 B1 | 9/2002 | Kroll | |
| 6,449,503 B1 | 9/2002 | Hsu | |
| 6,477,422 B1 | 11/2002 | Splett | |
| 6,480,734 B1 | 11/2002 | Zhang et al. | |
| 6,487,443 B2 | 11/2002 | Olson et al. | |
| 6,490,478 B1 | 12/2002 | Zhang et al. | |
| 6,522,917 B1 | 2/2003 | Hsu et al. | |
| 6,564,106 B2 | 5/2003 | Guck et al. | |
| 6,594,523 B1 | 7/2003 | Levine | |
| 6,611,713 B2 | 8/2003 | Schauerte | |
| 6,631,290 B1 | 10/2003 | Guck et al. | |
| 6,636,764 B1 * | 10/2003 | Fain et al. | 607/5 |
| 6,654,639 B1 | 11/2003 | Lu | |
| 6,684,100 B1 | 1/2004 | Sweeney et al. | |
| 6,708,058 B2 | 3/2004 | Kim et al. | |
| 6,731,982 B1 | 5/2004 | Kroll et al. | |
| 6,766,194 B1 | 7/2004 | Kroll | |
| 6,801,806 B2 | 10/2004 | Sun et al. | |
| 6,882,883 B2 | 4/2005 | Condie et al. | |
| 6,885,890 B2 | 4/2005 | Spinelli et al. | |
| 6,888,538 B2 | 5/2005 | Ely et al. | |
| 6,889,079 B2 | 5/2005 | Bocek et al. | |
| 6,909,916 B2 | 6/2005 | Spinelli et al. | |
| 6,922,585 B2 | 7/2005 | Zhou et al. | |
| 6,993,385 B1 | 1/2006 | Routh et al. | |
| 7,031,764 B2 | 4/2006 | Schwartz et al. | |
| 7,031,771 B2 | 4/2006 | Brown et al. | |
| 7,076,289 B2 | 7/2006 | Sakar et al. | |
| 7,085,599 B2 | 8/2006 | Kim et al. | |
| 7,103,405 B2 | 9/2006 | Sarkar et al. | |
| 7,107,098 B2 | 9/2006 | Sharma et al. | |
| 7,129,935 B2 | 10/2006 | Mackey | |
| 7,130,677 B2 | 10/2006 | Brown et al. | |
| 7,130,678 B2 | 10/2006 | Ritscher et al. | |
| 7,184,815 B2 | 2/2007 | Kim et al. | |
| 7,228,173 B2 | 6/2007 | Cazares | |
| 7,277,747 B2 | 10/2007 | Cazares et al. | |
| 7,328,063 B2 | 2/2008 | Zhang et al. | |
| 7,330,757 B2 | 2/2008 | Ostroff et al. | |
| 7,477,932 B2 | 1/2009 | Lee et al. | |
| 7,558,623 B2 | 7/2009 | Fischell et al. | |
| 7,756,578 B2 * | 7/2010 | Kim et al. | 607/14 |
| 2002/0183637 A1 | 12/2002 | Kim et al. | |
| 2003/0120316 A1 | 6/2003 | Spinelli et al. | |
| 2003/0191403 A1 | 10/2003 | Zhou et al. | |
| 2004/0088013 A1 | 5/2004 | Stadler et al. | |
| 2004/0093035 A1 | 5/2004 | Schwartz et al. | |
| 2004/0111119 A1 | 6/2004 | Sarkar et al. | |
| 2004/0111120 A1 | 6/2004 | Sarkar et al. | |
| 2004/0111121 A1 | 6/2004 | Brown et al. | |
| 2004/0167579 A1 | 8/2004 | Sharma et al. | |
| 2004/0176694 A1 | 9/2004 | Kim et al. | |
| 2004/0215092 A1 | 10/2004 | Fischell et al. | |
| 2004/0215270 A1 | 10/2004 | Ritscher et al. | |
| 2004/0254613 A1 | 12/2004 | Ostroff et al. | |
| 2005/0131476 A1 | 6/2005 | Kim et al. | |
| 2005/0137485 A1 | 6/2005 | Cao et al. | |
| 2005/0137641 A1 | 6/2005 | Naughton | |
| 2005/0192506 A1 | 9/2005 | Kim et al. | |
| 2005/0288600 A1 | 12/2005 | Zhang et al. | |
| 2006/0069322 A1 | 3/2006 | Zhang et al. | |
| 2006/0074331 A1 | 4/2006 | Kim et al. | |
| 2006/0111747 A1 | 5/2006 | Cazares et al. | |
| 2006/0217621 A1 | 9/2006 | Kim et al. | |
| 2006/0253044 A1 | 11/2006 | Zhang | |
| 2006/0281998 A1 | 12/2006 | Li | |
| 2007/0049974 A1 | 3/2007 | Li et al. | |
| 2007/0135848 A1 | 6/2007 | Kim et al. | |

FOREIGN PATENT DOCUMENTS

| EP | 0450943 A2 | 10/1991 |
|---|---|---|
| EP | 0547733 A2 | 6/1993 |
| EP | 0709112 | 5/1996 |
| EP | 0801960 A2 | 10/1997 |
| EP | 1112755 A1 | 7/2001 |
| EP | 1267993 A2 | 1/2003 |
| WO | WO-9840122 A1 | 9/1998 |
| WO | WO-0224276 A1 | 3/2002 |
| WO | WO-03047690 A2 | 6/2003 |
| WO | WO-2006039694 A2 | 4/2006 |

OTHER PUBLICATIONS

"U.S. Appl. No. 11/089,185, Final Office Action mailed Mar. 24, 2010", 7 pgs.

"U.S. Appl. No. 11/089,185, Final Office Action mailed Dec. 8, 2008", 7 pgs.

"U.S. Appl. No. 11/089,185, Non-Final Office Action mailed Mar. 28, 2008", 9 pgs.

"U.S. Appl. No. 11/089,185, Non-Final Office Action mailed May 15, 2009", 7 pgs.

"U.S. Appl. No. 11/089,185, Non-Final Office Action mailed Nov. 3, 2009", 7 pgs.

"U.S. Appl. No. 11/089,185, Notice of Allowability mailed Jul. 22, 2010", 4 pgs.

"U.S. Appl. No. 11/089,185, Notice of Allowance mailed Jun. 11, 2010", 4 pgs.

"U.S. Appl. No. 11/089,185, Response filed Jan. 27, 2010 to Non-Final Office Action mailed Nov. 3, 2009", 10 pgs.

"U.S. Appl. No. 11/089,185, Response filed Feb. 5, 2009 to Final Office Action mailed Dec. 8, 2008", 12 pgs.

"U.S. Appl. No. 11/089,185, Response filed Apr. 8, 2009 to Final Office Aciton mailed Dec. 8, 2008", 9 pgs.

"U.S. Appl. No. 11/089,185, Response filed May 20, 2010 to Final Office Action mailed Mar. 24, 2010", 11 pgs.

"U.S. Appl. No. 11/089,185, Response filed Jun. 24, 2008 to Non-Final Office Action mailed Mar. 28, 2008", 13 pgs.

"U.S. Appl. No. 11/089,185, Response filed Aug. 4, 2009 to Non-Final Office Action mailed May 15, 2009", 10 pgs.

"U.S. Appl. No. 11/276,213, Examiner Interview Summary mailed Jul. 27, 2009", 4 pgs.

"U.S. Appl. No. 11/276,213, Final Office Action Mailed Nov. 10, 2009", 8 pgs.

"U.S. Appl. No. 11/276,213, Non Final Office Action mailed May 6, 2009", 10 pgs.

"U.S. Appl. No. 11/276,213, Notice of Allowance mailed Mar. 2, 2010", 4 pgs.

"U.S. Appl. No. 11/276,213, Response filed Jan. 21, 2010 to Final Office Action mailed Nov. 10, 2009", 6 pgs.

"U.S. Appl. No. 11/276,213, Response filed Mar. 25, 2009 to Restriction Requirement mailed Feb. 27, 2009", 12 pgs.

"U.S. Appl. No. 11/276,213, Response filed Aug. 6, 2009 to Non Final Office Action mailed May 6, 2009", 11 pgs.

"U.S. Appl. No. 11/276,213, Restriction Requirement mailed Feb. 27, 2009", 7 pgs.

"Office Action from U.S. Appl. No. 11/209,976 dated Nov. 20, 2009", 11 pgs.

"VITALITY 2 Implantable Cardioverter Defibrillator System Guide", Guidant Corporation, (2004), cover pages and pp. 3-15 to 3-19.

Cazares, Shelley, "U.S. Appl. No. 10/995,655", (Nov. 23, 2004).

Cazares, Shelley Marie, et al., "U.S. Appl. No. 10/995,704", (Nov. 23, 2004).

Cazares, Shelley, et al., "U.S. Appl. No. 11/312,279", (Dec. 20, 2005).

Cazares, Shelley, et al., "U.S. Appl. No. 11/312,280", (Dec. 20, 2005).

Dubin, Dale, "Rapid Interpretation of EKG's", Cover Publishing Company, 6th Edition, (2000), 334-345.

Gold, Michael R., et al., "Advanced Rhythm Discrimination for Implantable Cardioverter Defibrillators Using Electrogram Vector Timing and Correlation", Journal of Cardiovascular Electrophysiology, vol. 13, No. 11, (Nov. 2002), 1092-1097.

Kerr, Martha, "Shock Rate Cut 70% with ICDs Programmed to First Deliver Antitachycardia Pacing: Results of the PainFREE Rx II Trial", NewsRhythms, MedScape CRM New, www.medscape.com, (2003), 2 pgs.

Kim, Jaeho, et al., "U.S. Appl. No. 10/955,831", (Sep. 30, 2004).

Lake, D E, et al., "Sample entropy analysis of neonatal heart rate variability", Am J Physiol Regul Integr Comp Physiol, 283(3), (2002), R789-797.

Li, Dan, "U.S. Appl. No. 11/038,996", (Jan. 20, 2005).

Li, Dan, "U.S. Appl. No. 11/151,102", (Jun. 13, 2005).

Li, Dan, et al., "U.S. Appl. No. 11/209,976", (Aug. 23, 2005).

Mercando, et al., "Measurement of Differences in Timing and Sequence Between Two Ventricular Electrodes as a Means of Tachycardia Differentiation", PACE, Part II, vol. 9, (Nov.-Dec. 1986), 1069-1078.

Richman, Joshua S, et al., "Physiological time-series analysis using approximate entropy and sample entropy", Am J Physiol Circ Physiol, vol. 278, (2000), H2039-H2049.

Wathen, Mark S., et al., "Shock reduction using antitachycardia pacing for spontaneous rapid ventricular tachycardia in patients with coronary artery disease", Circulation, 104(7), (Aug. 14, 2001), 796-801.

* cited by examiner

BLENDING CARDIAC RHYTHM DETECTION PROCESSES

CROSS-REFERENCE TO RELATED APPLICATIONS

This application is a Continuation of U.S. application Ser. No. 11/089,185, now issued as U.S. Pat. No. 7,818,056, filed on Mar. 24, 2005, the benefit of priority of which is claimed herein, and which is incorporated herein by reference in its entirety.

FIELD OF THE INVENTION

The present invention relates generally to implantable medical devices and, more particularly, to classifying, with an implantable medical device, cardiac rhythms produced by the heart.

BACKGROUND OF THE INVENTION

Proper cardiac function relies on the synchronized contractions of the heart at regular intervals. When normal cardiac rhythm is initiated at the sinoatrial node, the heart is said to be in sinus rhythm. However, due to electrophysiologic disturbances caused by a disease process or from an electrical disturbance, the heart may experience irregularities in its coordinated contraction. In this situation, the heart is denoted to be arrhythmic. The resulting cardiac arrhythmia impairs cardiac efficiency and can be a potential life threatening event.

Cardiac arrhythmias occurring in the atria of the heart, for example, are called supra-ventricular tachyarrhythmias (SVTs). SVTs take many forms, including atrial fibrillation and atrial flutter. Both conditions are characterized by rapid, contractions of the atria. Cardiac arrhythmias occurring in the ventricular region of the heart, by way of further example, are called ventricular tachyarrhythmias. Ventricular tachyarrhythmias (VTs), are conditions denoted by a rapid heart beat, 150 to 250 beats per minute, originating from a location within the ventricular myocardium.

Ventricular tachyarrhythmia can quickly degenerate into ventricular fibrillation (VF). Ventricular fibrillation is a condition denoted by extremely rapid, non synchronous contractions of the ventricles. This condition is fatal unless the heart is returned to sinus rhythm within a few minutes.

Implantable cardioverter/defibrillators (ICDs) have been used as an effective treatment for patients with serious tachyarrhythmias. ICDs are able to recognize and treat tachyarrhythmias with a variety of tiered therapies. These tiered therapies range from providing anti-tachycardia pacing pulses or cardioversion energy for treating tachyarrhythmias to high energy shocks for treating ventricular fibrillation. To effectively deliver these treatments, the ICD must first identify the type of tachyarrhythmia that is occurring, after which appropriate therapy may be provided to the heart.

For the reasons stated above, and for other reasons stated below which will become apparent to those skilled in the art upon reading the present specification, there is a need in the art for reliably and accurately recognize types of cardiac rhythms produced by the heart. The present invention fulfills these and other needs.

SUMMARY OF THE INVENTION

The present invention is directed to a method and system for classifying cardiac rhythms using an implantable device.

An embodiment of the invention involves a method for classifying a cardiac rhythm. The cardiac rhythm is classified using a classification process that includes a plurality of cardiac rhythm discriminators. Each rhythm discriminator provides an independent classification of the cardiac rhythm. The method determines if modifying the classification process is likely to enhance classification. If so, the classification process is modified and the rhythm is reclassified using the modified classification process.

Another embodiment of the invention is directed to device for classifying cardiac rhythms. The system includes a sensing circuit configured to sense cardiac signals associated with a cardiac rhythm. A plurality of independent rhythm discriminators are configured to provide an independent classification of the cardiac rhythm. The system further includes a classification processor coupled to the independent rhythm discriminators. The classification processor configured to implement a classification process to classify the cardiac rhythm, the classification process based on results of the independent rhythm discriminators. The classification processor is further configured to determine if modification of the classification process is likely to enhance rhythm classification and to modify the classification process if the rhythm classification is likely to be enhanced. The classification processor is configured to reclassify the cardiac rhythm using the modified classification process.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
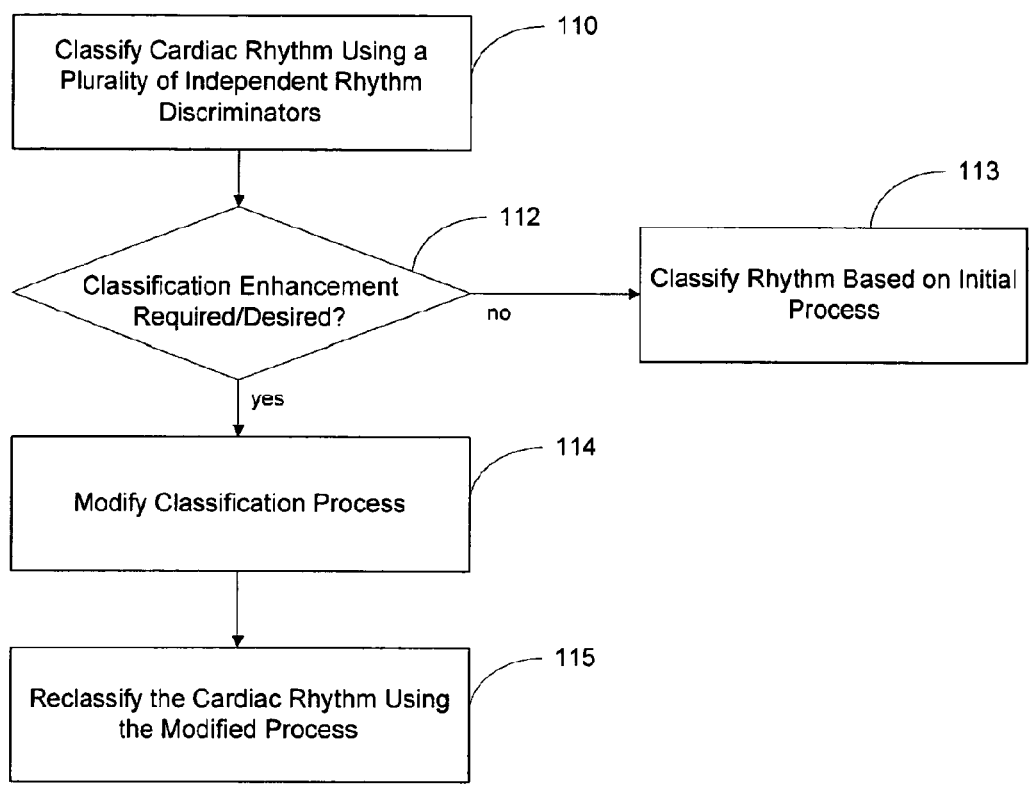
FIG. 1 is a flowchart illustrating a method of classifying a cardiac rhythm according to embodiments of the invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Cardiac therapy devices such as implantable cardiac defibrillators and/or cardioverters recognize various cardiac rhythms and provide treatment to convert, interrupt or mitigate dangerous rhythms. A tiered approach to therapy may be implemented, wherein some rhythms are treated with anti-tachycardia pacing (ATP), other rhythms are treated with high energy defibrillation shocks, and some arrhythmias are left untreated.

Appropriate treatment for cardiac arrhythmias may be selected based in part on the origin of the arrhythmia. For example, a fast, disorganized rhythm arising in a ventricle may be recognizable by an implantable cardiac device as ventricular fibrillation, a dangerous condition that requires immediate treatment. In this scenario, one or more defibrillation shocks may be applied to the heart to terminate the fibrillation and restore the heart to sinus rhythm.

If a ventricular rhythm is rapid but organized, and is associated with a relatively stable morphology, then a first therapy such as, anti-tachycardia pacing (ATP), may be delivered to the ventricles. If the ATP therapy is unsuccessful, then a different therapy may be delivered, such as one or more defibrillation shocks, may be delivered.

A fast rhythm arising in the atria, such as atrial fibrillation or atrial flutter, may be recognized by the device and may be treated with pacing or cardioversion shocks or may be left untreated. Fast atrial rhythms are generally not immediately life threatening and may not require treatment.

A number of cardiac rhythm discrimination procedures, denoted herein as rhythm discriminators, may be implemented in an implantable cardiac device or other therapy system to recognize the type of cardiac arrhythmia experienced by the patient. The embodiments of the invention presented herein are directed to systems and methods involving the use of a plurality of independent rhythm discriminators to recognize or classify various types of cardiac arrhythmia.

Classifying a cardiac rhythm using more than one independent rhythm discriminator may be desirable to increase the accuracy and/or sensitivity of the rhythm classification. However, the use of multiple discriminators adds complexity to the system that requires additional processing. For example, classification of the cardiac rhythm using multiple independent discriminators may produce conflicting classification results. Modification of the classification process, such as by using additional information acquired by other device processes, by modifying parameters of the initially used discriminators, by employing additional discriminators, or by other procedures, may be required or desired to resolve conflicts between classification results.

Further, enhancement of the rhythm classification process may be desirable even though the independent discriminators do not produce conflicting classifications. The device may be capable of recognizing if modification of the classification process is likely to enhance classification and modifying the classification process. For example, enhancement of the classification process may be desirable if the one or more discriminators are produce an indeterminate or borderline classification result. In this scenario, the device may enhance classification by modifying the classification process. The classification process may be modified, for example, by using additional information acquired by other device processes, by modifying parameters of the initially used discriminators, by employing additional discriminators, or by other procedures.

The flowchart of FIG. 1 illustrates a method of classifying a cardiac rhythm according to embodiments of the invention. Initially, the cardiac rhythm is classified 110 using a plurality of independent rhythm discriminators. The rhythm discriminators may classify a cardiac rhythm based on various characteristics of the cardiac rhythm including, for example, the rate of the cardiac rhythm, intervals between successive atrial and/or ventricular beats, and the morphology of sensed cardiac signals associated with cardiac beats of the rhythm. The rhythm discriminators typically utilize one or more parameters that may be programmable by the physician and/or alterable by the device.

After the cardiac rhythm has been classified 110 by the initial process using the independent rhythm discriminators, the device determines 112 if enhancement of the rhythm classification is required or desired. If rhythm classification enhancement is not desired, then the cardiac rhythm is classified 113 based on the initial classification process. For example, in one scenario, the device may implement enhanced rhythm classification if two of the cardiac rhythm discriminators used in the initial rhythm classification process return conflicting classifications. In another scenario, the device may implement enhanced rhythm classification if one or more of the rhythm discriminators was unable to classify the cardiac rhythm and returned an indeterminate result. In yet another scenario, the device may implement enhanced rhythm classification if the initial rhythm discriminators returned borderline classification results and additional and/or modified processing may be desired or required to confirm the initial classification.

If enhanced rhythm classification is implemented, then the process for performing the rhythm classification may be modified 114 and the rhythm is reclassified 115 using the modified classification process. In various embodiments described in greater detail below, modification of the classification processes may involve modifying one or more parameters associated with a particular rhythm discriminator, acquiring additional information acquired by other functions of the cardiac device to aid in the classification processes, initiating additional rhythm discriminators to enhance the rhythm classification and/or by other procedures.

Figure 2:
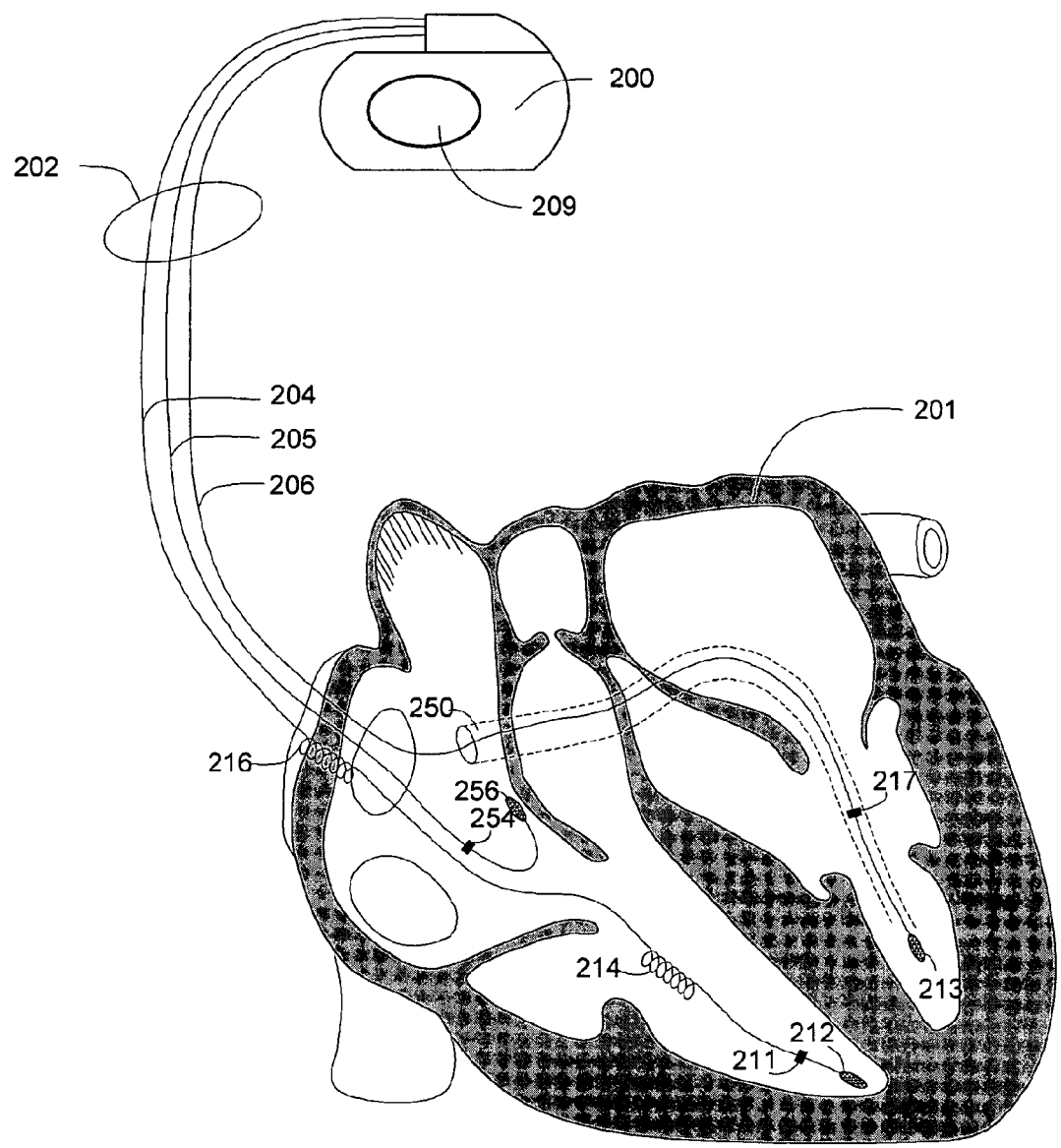
FIG. 2 is a partial view of a cardiac rhythm management (CRM) device that may be used to implement arrhythmia classification and therapy in accordance with embodiments of the invention.

FIG. 2 is a partial view of a cardiac rhythm management (CRM) device that may be used to implement rhythm classification and arrhythmia therapy in accordance with embodiments of the invention. Methods of the invention may be implemented in a variety of implantable or patient-external cardiac therapeutic and/or diagnostic devices including, for example, pacemakers, defibrillators, cardioverters, bi-ventricular pacemakers, and/or cardiac resynchronization devices, among others. The CRM device illustrated in FIG. 2 includes an implantable housing 200 containing circuitry electrically coupled to an intracardiac lead system 202. Portions of the implantable housing may be configured as a can electrode 209. The housing 200 and the intracardiac lead system 202 is implanted in a human body with portions of the intracardiac lead system 202 inserted into a heart 201. The intracardiac lead system 202 is used to detect electric cardiac signals produced by the heart 201 and to provide electrical energy to the heart 201 under predetermined conditions to treat cardiac arrhythmias.

The intracardiac lead system 202 includes one or more electrodes used for pacing, sensing, and/or defibrillation. In the particular embodiment shown in FIG. 2, the intracardiac lead system 202 includes a right ventricular lead system 204, a right atrial lead system 205, and a left ventricular lead system 206. In one embodiment, the right ventricular lead system 204 is configured as an integrated bipolar pace/shock lead.

The right ventricular lead system 204 includes an SVC-coil 216, an RV-coil 214, and an RV-tip electrode 212. The RV-coil 214, which may alternatively be configured as a separate defibrillation coil and an RV-ring electrode 211, is spaced apart from the RV-tip electrode 212, which is a pacing electrode for the right ventricle.

The right atrial lead system 205 includes a RA-tip electrode 256 and an RA-ring electrode 254. The RA-tip 256 and RA-ring 254 electrodes may provide pacing pulses to the right atrium of the heart and may also be used to detect cardiac signals from the right atrium. In one configuration, the right atrial lead system 205 is configured as a J-lead.

In the configuration of FIG. 2, portions of the intracardiac lead system 202 are shown positioned within the heart 201, with the right ventricular lead system 204 extending through the right atrium and into the right ventricle. Typical locations for placement of the RV-tip electrode 212 are at the right ventricular (RV) apex or the RV outflow tract.

In particular, the RV-tip electrode 212 and RV-coil electrode 214 are positioned at appropriate locations within the right ventricle. The SVC-coil 216 is positioned at an appropriate location within a major vein leading to the right atrium chamber of the heart 201. The RV-coil 214 and SVC-coil 216 depicted in FIG. 2 are defibrillation electrodes.

The left ventricular lead system 206 is advanced through the superior vena cava (SVC), the right atrium 220, the ostium of the coronary sinus, and the coronary sinus 250. The left ventricular lead system 206 is guided through the coronary sinus 250 to a coronary vein of the left ventricle. This vein is used as an access pathway for leads to reach the surfaces of the left atrium and the left ventricle which are not directly accessible from the right side of the heart. Lead placement for the left ventricular lead system may be achieved via subclavian vein access and a preformed guiding catheter for insertion of the left ventricular (LV) electrodes 213 and 217 adjacent the left ventricle. In one configuration, the left ventricular lead system 206 is implemented as a single-pass lead.

An LV distal electrode 213, and an LV proximal electrode 217 may be positioned adjacent to the left ventricle. The LV proximal electrode 217 is spaced apart from the LV distal electrode, 213 which is a pacing electrode for the left ventricle. The LV distal 213 and LV proximal 217 electrodes may also be used for sensing the left ventricle.

The lead configurations illustrated in FIG. 2 represent one illustrative example. Additional lead/electrode configurations may include additional and/or alternative intracardiac electrodes and/or epicardial electrodes. For example, in one configuration, an extracardiac lead may be used to position epicardial electrodes adjacent the left atrium for delivering electrical stimulation to the left atrium and/or sensing electrical activity of the left atrium.

Figure 3:
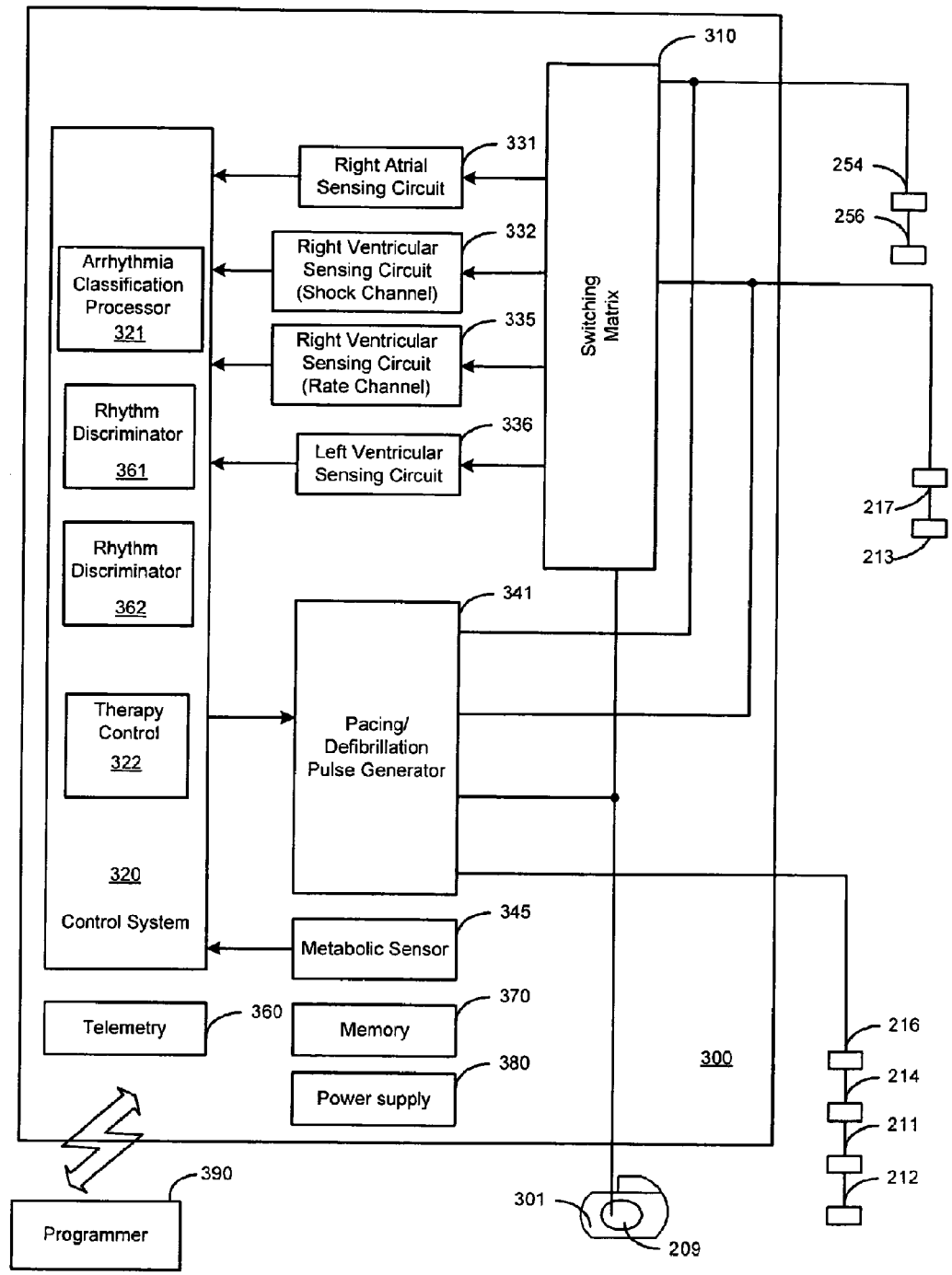
FIG. 3 is a block diagram of a cardiac rhythm management (CRM) device 300 suitable for implementing arrhythmia classification and therapy delivery in accordance with embodiments of the invention.

Referring now to FIG. 3, there is shown a block diagram of a cardiac rhythm management (CRM) device 300 suitable for implementing arrhythmia classification in accordance with embodiments of the invention. FIG. 3 shows a CRM device 300 divided into functional blocks. It is understood by those skilled in the art that there exist many possible configurations in which these functional blocks can be arranged. The example depicted in FIG. 3 is one possible functional arrangement. Various functions of the CRM device 300 may be accomplished by hardware, software, or a combination of hardware and software.

The CRM device 300 includes components for sensing cardiac signals from a heart and delivering therapy, e.g., pacing pulses or defibrillation shocks, to the heart. The circuitry of the CRM device 300 may be encased and hermetically sealed in a housing 301 suitable for implanting in a human body. Power to the circuitry is supplied by an electrochemical battery power supply 380 that is enclosed within the housing 301. A connector block with lead terminals (not shown) is additionally attached to housing 301 to allow for the physical and electrical attachment of the intracardiac lead system conductors to the encased circuitry of the CRM device 300.

In one embodiment, the CRM device 300 comprises programmable microprocessor-based circuitry, including control circuitry 320, a memory circuit 370, sensing circuitry 331, 332, 335, 336, and a pacing/defibrillation pulse generator 341. Components of the CRM device 300 cooperatively perform operations involving arrhythmia classification according to the approaches of the present invention. The control circuitry 320 is responsible for arrhythmia detection, classification, and therapy control. The control circuitry 320 may encompass various functional components, for example, independent rhythm discriminators 361, 362, an arrhythmia classification processor 321 and a therapy control unit 322.

The memory circuit 370 may store program instructions used to implement the functions of the CRM device 300 as well as data acquired by the CRM device 300. For example, the memory circuit 370 may store historical records of sensed cardiac signals, including arrhythmic episodes, and/or information about therapy delivered to the patient. The memory circuit 370 may also store morphology templates representative of cardiac beats associated with various types of cardiac rhythms.

The historical data stored in the memory 370 may be used for various purposes, including diagnosis of patient diseases or disorders. Analysis of the historical data may be used to adjust the operations of the CRM device 300. Data stored in the memory 370 may be transmitted to an external programmer unit 390 or other computing device, such as an advanced patient management system as needed or desired.

Telemetry circuitry 360 allows the CRM device 300 to communicate with an external programmer unit 390 and/or other remote devices. In one embodiment, the telemetry circuitry 360 and the external programmer unit 390 use a wire loop antenna and a radio frequency telemetric link to receive and transmit signals. In this manner, programming commands and data may be transferred between the CRM device 300 and the external programmer 390 after implant.

The CRM device 300 may function as a pacemaker and/or a defibrillator. As a pacemaker, the CRM device 300 delivers a series of electrical stimulations to the heart to regulate heart rhythm. Therapy control circuitry 322 controls the delivery of pacing pulses to treat various arrhythmic conditions of the heart, for example. In various embodiments, the CRM device 300 may deliver pacing pulses to one or more of the right atrium, left atrium, right ventricle and the left ventricle. The heart may be paced to treat bradycardia, or to synchronize and/or coordinate contractions of the right and left ventricles.

For example, right ventricular pacing may be implemented using unipolar or bipolar configurations. Unipolar RV pacing involves, for example, pacing pulses delivered between the RV-tip 212 to can 209 electrodes. Bipolar pacing involves, for example, delivery of pacing pulses between the RV-tip 212 to RV-coil 214 electrodes. If an RV-ring electrode is present, bipolar pacing may be accomplished by delivering the pacing pulses to the RV-tip 212 and RV-ring 211 electrodes.

Left ventricular pacing may be implemented using unipolar or bipolar configurations. Unipolar LV pacing may include, for example, pacing pulses delivered between the LV distal electrode 213 and the can 209. Alternatively, bipolar LV pacing may be accomplished by delivering the pacing pulses using the LV distal electrode 213 and the LV proximal electrode 217.

Similarly, unipolar (RA-tip electrode 256 to can electrode 209) atrial pacing or bipolar (RA-tip electrode 256 to RA-ring electrode 254) atrial pacing may be provided by the CRM device 300.

The CRM device 300 may also provide tachyarrhythmia therapy. For example, tachyarrhythmia therapy may be provided in the form of anti-tachycardia pacing (ATP) pulses delivered to the heart. The ATP pulses may involve a series of timed paces of programmable width and amplitude that are implemented to interrupt a tachyarrhythmia episode. The ATP therapy may involve, for example, burst pacing at about 25 Hz to about 50 Hz. In various implementations, the pace-to-pace interval may have a variable or constant length. For immediately life threatening arrhythmias, such as ventricular fibrillation, the therapy control circuitry 322 may control the delivery of one or a series of defibrillation shocks to the heart to terminate the fibrillation.

In the embodiment depicted in FIG. 3, electrodes RA-tip 256, RA-ring 254, RV-tip 212, RV-ring 211, RV-coil 214, SVC coil 216, LV distal electrode 213, LV proximal electrode 217, and can 209 are coupled through a switching matrix 310 to various sensing circuits 331, 332, 335, 336. A right atrial sensing channel circuit 331 serves to sense and amplify electrical signals from the right atrium of the heart. For example, bipolar sensing in the right atrium may be implemented by sensing signals developed between the RA-tip 256 and RA-ring 254 electrodes. The switch matrix 310 may be operated to couple the RA-tip 256 and RA-ring 254 electrodes to the RA sensing channel circuit 331 to effect bipolar sensing of right atrial signals. Alternatively, unipolar right atrial sensing may be accomplished by operating the switch matrix 310 to couple the RA-tip 256 and can 209 electrodes to the RA sensing channel circuit 331.

Cardiac signals sensed through the use of the RV-tip electrode 212 and RV-coil 214 or RV-ring electrode 211 are right ventricular (RV) near-field signals and are referred to as RV rate channel signals herein. Bipolar rate channel sensing may be accomplished by operating the switch matrix 310 to couple the RV-tip electrode 212 and the RV-coil 214 electrode or the RV-ring electrode 211 through the RV rate channel sensing circuitry 335. The rate channel signal may be detected, for example, as a voltage developed between the RV-tip electrode 212 and the RV-coil 214 electrode or the RV-ring electrode 211. The RV rate channel sensing circuitry 335 serves to sense and amplify the RV rate channel signal.

Unipolar RV sensing may be implemented, for example, by coupling the RV-tip 212 and can 209 electrodes to the RV rate channel sensing circuitry 335. In this configuration, the rate channel signal is detected as a voltage developed between the RV-tip 212 to can 209 sensing vector.

The RV lead system may also include an RV-ring electrode 211 used for bipolar pacing and sensing. If an RV-ring electrode is included in the lead system, bipolar sensing may be accomplished by sensing a voltage developed between the RV-tip 212 and RV-ring 211 electrodes.

Far-field signals, such as cardiac signals sensed through use of defibrillation coils or electrodes 214, 216, 209, are referred to as morphology or shock channel signals herein. The shock channel signal may be detected as a voltage developed between the RV-coil 214 to the can electrode 209, the RV-coil 214 to the SVC-coil 216, or the RV-coil 214 to the can electrode 209 shorted to the SVC-coil 216. The switch matrix 310 is operated to couple the desired shock channel sensing vector, e.g., RV-coil to can, to the right ventricular shock channel sensing circuitry 332. The RV shock channel sensing circuitry 332 serves to sense and amplify the shock channel signal.

The outputs of the switching matrix 310 may also be operated to couple selected combinations of the electrodes to LV sensing channel circuitry 336 for sensing electrical activity of the left ventricle. Bipolar left ventricular sensing may be accomplished by operating the switch matrix 310 to couple the LV-distal 213 and the LV proximal electrodes 217 through the LV channel sensing circuitry 336. In this configuration, the LV signal is detected as a voltage developed between the LV proximal and LV distal electrodes.

Unipolar LV sensing may be implemented, for example, by coupling the LV distal 213 and can 209 electrodes to the LV sensing circuitry 336. In this configuration, the LV signal is detected as a voltage developed between the RV-tip 212 to can 209 sensing vector.

The CRM device 300 includes a plurality of independent rhythm discriminators 361, 362 and an arrhythmia classification processor 321 coupled to the rhythm discriminators and configured to classify a variety of cardiac rhythms, including ventricular or atrial arrhythmias. The arrhythmia classification processor 321 may detect and/or classify arrhythmias using the results from the plurality of independent discriminators 361, 362. The arrhythmia classification processor evaluates the results of the independent discriminators 361, 362 and determines if modification of the classification process is likely to enhance classification of the rhythm. If so, the arrhythmia classification processor modifies the process and reclassifies the cardiac rhythm based on the modified process. Modification of the process may involve further evaluation of the cardiac rhythm using the independent rhythm discriminators 361, 362, or other processes.

The rhythm discriminators 361, 362 may include, for example, one or more discriminators that operate by analyzing the heart rate of atrial or ventricular chambers. It will be appreciated that heart rate may be evaluated by evaluating the intervals between successive cardiac events, such as A-A intervals (intervals between successive atrial events), V-V intervals (intervals between successive ventricular events), A-V intervals (intervals between an atrial event and a subsequent ventricular event) and/or V-A intervals (intervals between a ventricular event and a subsequent atrial event).

One or more rhythm discriminators may utilize intervals between successive cardiac events to evaluate, for example, the onset of a cardiac arrhythmic episode, the stability of the atrial and/or ventricular rhythms, and/or the duration of an arrhythmic episode.

One or more rhythm discriminators may evaluate the morphology of individual cardiac beat signals of the arrhythmic episode to classify the arrhythmia. Cardiac beats associated with arrhythmias originating the in the atria may be discerned from cardiac beats associated with arrhythmias originating in the ventricles based on the morphology characteristics of the cardiac beat signals.

A morphology-based discriminator may compare the cardiac beat signals to one or more morphology templates. The morphology templates characterize cardiac beat signals that are representative of a particular type of rhythm. In one implementation, the morphology-based discriminator may compare one or more cardiac beat signals of an arrhythmia episode to a morphology template characterizing a supraventricular rhythm (SVR). If the cardiac beat signals are not similar to the SVR template, then the arrhythmic episode is recognized as an arrhythmia of ventricular origin. If the cardiac beat signals are similar to the SVR template, then the arrhythmic episode is recognized as an arrhythmia of non-ventricular origin.

If the results of the independent rhythm discriminators 361, 362 conflict, are indeterminate, or are borderline, the arrhythmia classification processor 321 may operate to implement modifications to the classification process to enhance classification.

Based on the arrhythmia classification determined by the arrhythmia classification processor 321, the therapy control may initiate an appropriate therapy, to terminate or mitigate the arrhythmia. The therapy may include ATP, cardioversion and/or defibrillation shocks, for example. For some types of arrhythmia, therapy may not be appropriate, in which case therapy may be withheld.

The CRM device 300 may incorporate one or more metabolic sensors 345 for sensing the activity and/or hemodynamic need of the patient. Rate-adaptive pacemakers typically utilize metabolic sensors to adapt the pacing rate to match the patient's hemodynamic need. A rate-adaptive pacing system may use an activity or respiration sensor to determine an appropriate pacing rate. Patient activity may be sensed, for example, using an accelerometer disposed within the housing of the pulse generator. Transthoracic impedance, which may be measured, for example, via the intracardiac electrodes, may be used to determine respiration rate. Sensor information from the metabolic sensor is used to adjust the pacing rate to support the patient's hemodynamic need. If the sensors indicate the patient's activity and/or respiration rate is high, then the patient's pacing rate is increased to correspond to the level of activity or rate of respiration.

Figure 4:
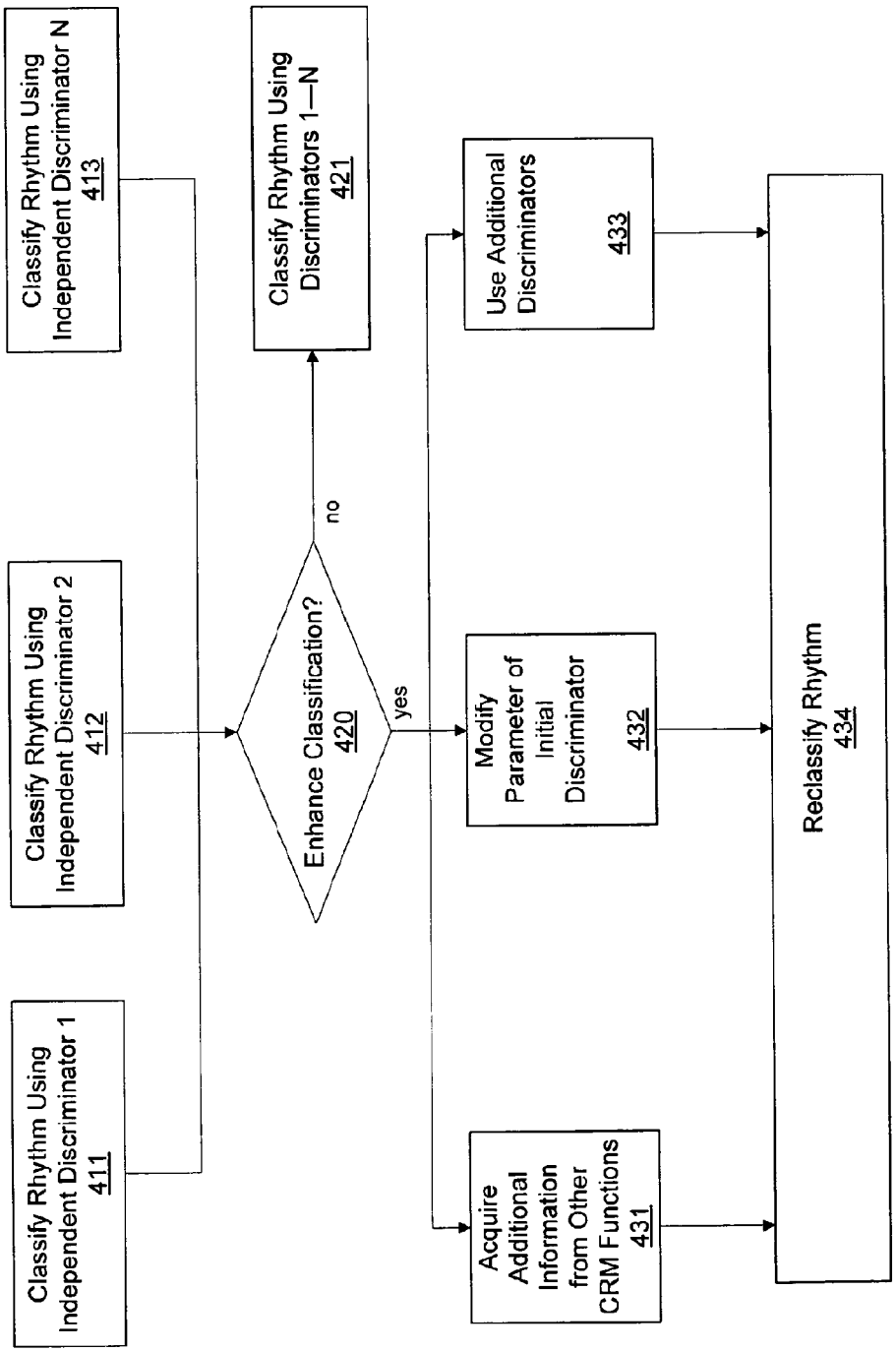
FIG. 4 is a flow diagram illustrating a method of classifying a cardiac rhythm in accordance with embodiments of the invention.

FIG. 4 is a flow diagram illustrating a method of classifying a cardiac rhythm in accordance with embodiments of the invention. The system initially classifies 411, 412, 413 the cardiac rhythm using a plurality of independent rhythm discriminators. For example, the independent discriminators used in the initial rhythm classification process may analyze cardiac rates, interval patterns and/or the morphology of cardiac signals associated with one or more beats of the arrhythmic episode.

Following the initial classification by the independent discriminators 411, 412, 413, the system may implement 420 rhythm classification enhancement. If the rhythm classification is not enhanced, then the cardiac rhythm is classified 421 based on the results of the initial rhythm discriminators 411, 412, 413. If the rhythm classification enhancement is implemented 420, then one or more additional rhythm discrimination procedures 431, 432, 433 may be utilized to enhance classification of the cardiac rhythm.

For example, the system may implement 420 rhythm classification enhancement if two or more of the initial rhythm discriminators 411, 412, 413 produce conflicting results. A conflict situation may arise, for example, if a first rhythm discriminator classifies the cardiac rhythm as an SVT and a second rhythm discriminator classifies the cardiac rhythm as a VT.

In another example, the system may implement 420 rhythm classification enhancement if one or more of the initial discriminators 411, 412, 413 are unable to classify the cardiac rhythm. In this situation, the initial rhythm discriminators 411, 412, 413 may return a result indicating that the cardiac rhythm is unknown or is unclassifiable.

In yet another example, the system may implement 420 rhythm classification enhancement if one or more of the initial discriminators classify the cardiac rhythm, but the classification is within a borderline range. For example, one or more of the initial discriminators may classify the rhythm as one type of arrhythmia, e.g., SVT, but the classification is within a borderline range of being classified as a VT. In this situation, a more definitive classification may be possible by performing one or more of the additional discrimination procedures 432, 432, 433 and reclassifying 434 the cardiac rhythm.

FIG. 4 illustrates three exemplary rhythm discrimination procedures that may be employed to enhance the rhythm classification. Other discrimination procedures are possible, and the invention is not limited to the three examples illustrated in FIG. 4. Additional discrimination procedures used to enhance rhythm classification may involve, for example, acquiring additional information 431 from other CRM device functions. Cardiac rhythm management devices are often equipped with a number of sensors that may be used for diagnostic or therapeutic purposes. Sensor information acquired from such sensor components may be used in connection with cardiac rhythm classification.

In one configuration, a CRM device may incorporate an activity sensor that generates a signal corresponding to the patient's level of activity. The sensor signal may be used by the CRM device to deliver a hemodynamically appropriate pacing therapy to the patient. Information from the activity sensor and/or other sensors or systems of the CRM device may be utilized to enhance rhythm classification such as by discriminating between a physiologic sinus tachycardia and a pathologic arrhythmia. For example, if the patient's heart rate is relatively high and the activity sensor output indicates that the patient is also very active, then the rhythm discriminator 431 may classify the cardiac rhythm as physiologic sinus tachycardia caused by elevated patient activity.

The additional discrimination procedures employed for enhanced rhythm classification may involve 432 modifying a parameter of one or more of the initial rhythm discriminators 411-413 initially used for the rhythm classification. Alternatively or additionally, one or more supplementary discriminators may be utilized 433 for rhythm classification. Following implementation of the additional discriminators 431, 432, 433, the cardiac rhythm is reclassified 434 based on the information from the initial discriminators 411, 412, 413, information from other device functions 431, information from the modified discriminators 432, and/or information from additional discrimination procedures 433.

The rhythm classification enhancements 431, 432, 433 may be used alone or in combination. For example, the device may implement one of the rhythm classification enhancements 431, 432, 433 before reclassifying the cardiac rhythm 434, or may implement a plurality of the rhythm classification enhancements 431, 432, 433 before reclassification 434. If a plurality of the rhythm classification enhancements 431, 432, 433 are implemented, then the device may implement the rhythm classification enhancements 431, 432, 433 in parallel or serially.

Figure 5A:
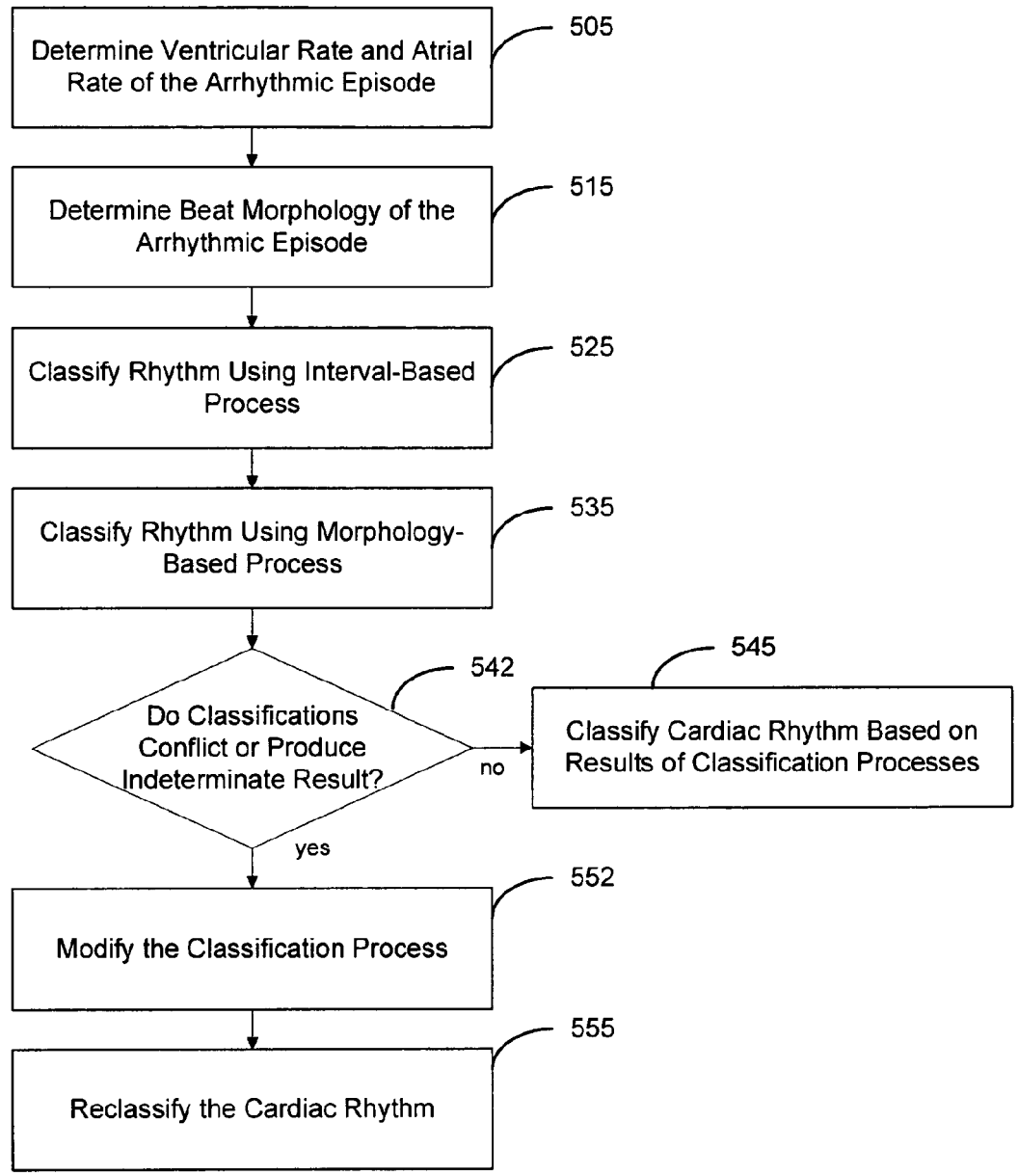
FIG. 5A is a flowchart illustrating classification of a cardiac rhythm using multiple independent discriminators in accordance with embodiments of the invention.

FIG. 5A is a flowchart illustrating a method of rhythm classification in accordance with embodiments of the invention. In this embodiment, two independent discriminators are initially used to classify the cardiac rhythm. One initial discriminator comprises an interval-based discriminator that utilizes the relationship between the atrial rate and the ventricular rate to classify the cardiac rhythm. Another initial discriminator comprises a morphology-based discriminator that evaluates the morphology of the cardiac beats of the arrhythmic episode for rhythm classification.

In accordance with this embodiment, the device measures 505 the ventricular rate and the atrial rate of an arrhythmic episode. For example the ventricular and atrial rates may be expressed in terms of average rates of a number of cardiac beats of the arrhythmic episode. The morphology of the beats of the arrhythmic episode is determined 515.

The rhythm is classified 525 using an interval-based process. The rhythm is classified 535 using a morphology-based process. If the results of the two initial rhythm classifications are not 542 in conflict and produce definite results, then the cardiac rhythm may be classified 545 based on the results of the initial discriminators. However, if the results of the initial discriminators conflict or if one or both of the initial discriminators produce indeterminate or borderline results 542, then the classification process may be modified 552 and the rhythm reclassified 555 using the modified process.

An independent discriminator may incorporate a multiplicity of discrimination processes that may be used for rhythm discrimination. For example, an interval-based discriminator may examine one or more of the rhythm onset, stability and/or the relationship between the atrial rate (A-rate) and the ventricular rate (V-rate) to classify the cardiac rhythm.

Comparison of the A-rate to the V-rate may provide insight into the origin of the arrhythmia. For example, if the A-rate is greater than the V-rate, the origin of the rhythm is more likely to be atrial in origin. Thus, if the A-rate is greater than the V-rate, the rhythm may be classified as SVT. However, if the V-rate rate is greater than the A-rate, then the origin of the arrhythmia is more likely ventricular in origin and the rhythm may be classified as a VT. If there is roughly a one-to-one correspondence between the atrial and ventricular rates, then the system may not be able to classify the type of rhythm based the A rate and V rate relationship. However, classifications based solely on the relationship between the atrial and ventricular rates may produce incorrect results, particularly if the difference between atrial and ventricular rates is small.

In one configuration if the average rate of the last N, e.g. about 10, ventricular intervals is compared to the average rate of the last N atrial intervals. If the average ventricular rate is greater than the average atrial rate by at least a predetermined time such as about 10 bpm, then the rhythm is determined to be a ventricular rhythm and appropriate therapy, such as ATP or defibrillation, may be delivered. If the ventricular rate is less than the atrial rate, then therapy may be withheld because the system determines that the rhythm is SVT.

Stability analysis may comprise an interval-based process used to distinguish unstable or irregular rhythms from stable rhythms. Stability analysis may be accomplished by measuring the degree of variability in the cardiac cycles, e.g., the V-V intervals between sensed R-waves. The degree of variability may allow the system to distinguish conducted atrial fibrillation (AF), which may produce greater V-V variability, from monomorphic VT, which is typically stable. Stability analysis may also be used to differentiate monomorphic VT from polymorphic VT. Distinguishing monomorphic VT from polymorphic VT may be used in determining an appropriate treatment. For example, monomorphic VT may be treated using ATP, whereas polymorphic VT may be more successfully treated using defibrillation shocks. Methods for recognizing and treating various types of monomorphic VT are described in the following commonly owned U.S. patent application Ser. No. 10/955,831, filed Sep. 30, 2004, Ser. No. 10/996,340, filed Nov. 23, 2004, Ser. No. 995,705, filed Nov. 23, 2004, and Ser. No. 10,995,655, filed Nov. 23, 2004 which are incorporated herein by reference.

In one embodiment, the stability analysis algorithm calculates V-V interval differences and determines an average difference between V-V intervals. After a period of time, which may correspond, for example, to the duration interval discussed herein, the system evaluates the rhythm stability by comparing the current average difference to a stability threshold. If the average difference is greater than the stability threshold, the rhythm is determined to be unstable. Instability in the cardiac rhythm is an indication that the arrhythmia is atrial in origin (SVT).

The onset of the cardiac rhythm may be considered in classifying an arrhythmia. The onset criterion is particularly useful in discriminating between sinus tachycardia and ventricular tachyarrhythmia. The onset parameter of the cardiac rhythm represents a measurement of how quickly the rhythm transitions from a slow rate to a faster rate. The onset of the rhythm may be examined to differentiate between physiologic sinus tachycardias, which typically begin slowly, from pathologic tachycardias, which typically begin suddenly. If the rate increase is gradual, the system may determine that a fast rhythm cardiac rhythm is sinus tachycardia and withhold therapy. However, if the rate abruptly increases, it is more likely that the rhythm is a pathologic rhythm and the system may deliver an appropriate therapy to terminate or mitigate the arrhythmia.

The above rhythm discrimination techniques rely on examining the intervals between a number of cardiac beats to determine various parameters of the cardiac rhythm including atrial and ventricular rates, onset, and/or stability. An alternative rhythm analysis may involve examining the morphological characteristics of the electrical signals associated with one or more beats of the arrhythmic episode. In one example, various characteristics of a cardiac beat signal, e.g., number of peaks, peak polarity, peak area, and/or sequence of feature points may be compared to a template, such as a template representative of a supraventricular rhythm (SVR). If the morphology of one or more of the cardiac beat signals of the arrhythmic episode are consistent with the SVR template then the arrhythmia is determined to be SVT. However, if one or more of the cardiac beat signals of the arrhythmic episode are inconsistent with the SVR template, then the arrhythmia is determined to be VT.

A cardiac signal may be considered to be consistent with a template if the features, samples, or other morphological characteristics of the cardiac signal are determined to be sufficiently similar to the corresponding template features, samples, or morphological characteristics. If a cardiac signal is sufficiently similar to a template representative of a particular type of cardiac beat, e.g., and SVR beat, then the cardiac signal may be classified as the particular type of beat. Various techniques may be used to compare a template and a cardiac signal, including the correlation techniques described herein.

Rhythm classification by morphology analysis may involve comparing features points of one or more cardiac beat signals of an arrhythmic episode to corresponding feature points of a template representative of an SVR beat. In one implementation, acquisition and use of templates for morphology analysis may be accomplished using a two channel approach. Cardiac beats are sensed on ventricular rate channel and a ventricular shock channel. In this example, a feature of the rate channel signal, e.g., the rate channel R-wave peak, may be used as a fiducial point to align the shock channels signals of multiple cardiac beats with the morphology template.

Figure 5B:
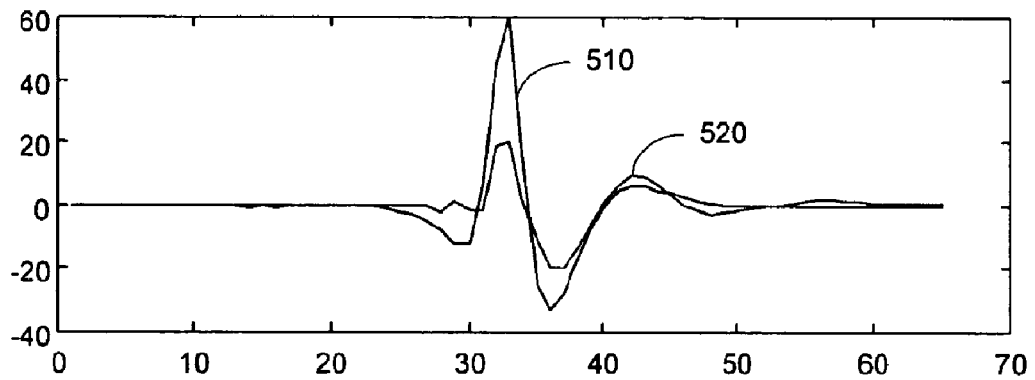
FIGS. 5B and 5C are graphs illustrating the process of rate and shock channel alignment used in morphology-based discriminator in accordance with embodiments of the invention.
Figure 5C:
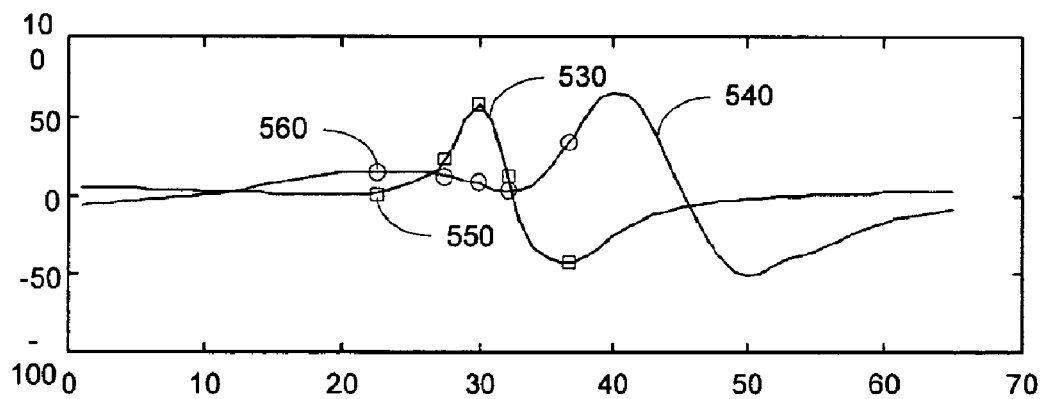

FIGS. 5B and 5C illustrate the process of shock signal alignment. FIG. 5B illustrates aligned rate channel signals of a template (SVR) beat 510 and a VT beat 520, respectively. FIG. 5C illustrates the aligned shock channel signals of the template beat 530 and the VT beat 540.

The template may comprise a sequence of feature points of a shock channel signal representative of a particular type of rhythm. For example, with reference to FIG. 5C, a number of feature points 550 may be selected based as a template representative of the SVR beat. Samples 560 of the aligned shock channel beat 540 are compared to corresponding template samples 550. The cardiac beat may be recognized as the type of cardiac rhythm represented by the template if the cardiac beat samples are similar to the template samples.

The similarity between the cardiac beat signal and the template may be compared by determining the correlation between the cardiac beat signal samples and the template features. For example, the correlation between the template and a cardiac beat may be expressed in terms of a feature correlation coefficient (FCC). In one particular embodiment, Equation 1, provided below, is used to compute the FCC between the template features and the beat features.

$$FCC = \frac{\left(N\sum_{i=1}^{N} X_i Y_i - \left(\sum_{i=1}^{N} X_i\right)\left(\sum_{i=1}^{N} Y_i\right)\right)^2}{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)} \quad [1]$$

where, Xi represents template N features and Yi represents beat N features, and N=8 in this illustrative example. The sign of the numerator term is checked before squaring. If the numerator is negative, the beat is uncorrelated, and the remainder of the computation need not be performed.

Alternatively, a generalized equation may be used for computation of a correlation coefficient in accordance with a correlation waveform analysis (CWA) technique. An equation for calculation of the correlation coefficient (CC) using this technique is set forth in Equation 2.

$$CC = \frac{N\sum_{i=1}^{N} X_i Y_i - \left(\sum_{i=1}^{N} X_i\right)\left(\sum_{i=1}^{N} Y_i\right)}{\sqrt{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)}} \quad [2]$$

where, Xi represents template N samples and Yi represents signal N samples in this illustrative example. Methods and systems involving the use of a morphology template for determining cardiac rhythms, aspects of which may be implemented by the embodiments discussed herein, are described in commonly owned U.S. Pat. No. 6,449,503 which is incorporated herein by reference.

The system may examine the duration of the cardiac rhythm in the classification process. If the arrhythmia is a non-sustained or self-terminating rhythm, then therapy delivery may be avoided. For example, the system may trigger a duration timer when a fast ventricular rhythm is detected. The duration timer may be programmable to time an interval of about 1 second to about 60 seconds, for example. Each cardiac cycle, the system checks for a timeout of the duration timer. If the fast cardiac rate persists throughout the duration timer interval, then the duration requirement of the rhythm classification is met and the system may initiate therapy.

Figure 6A:
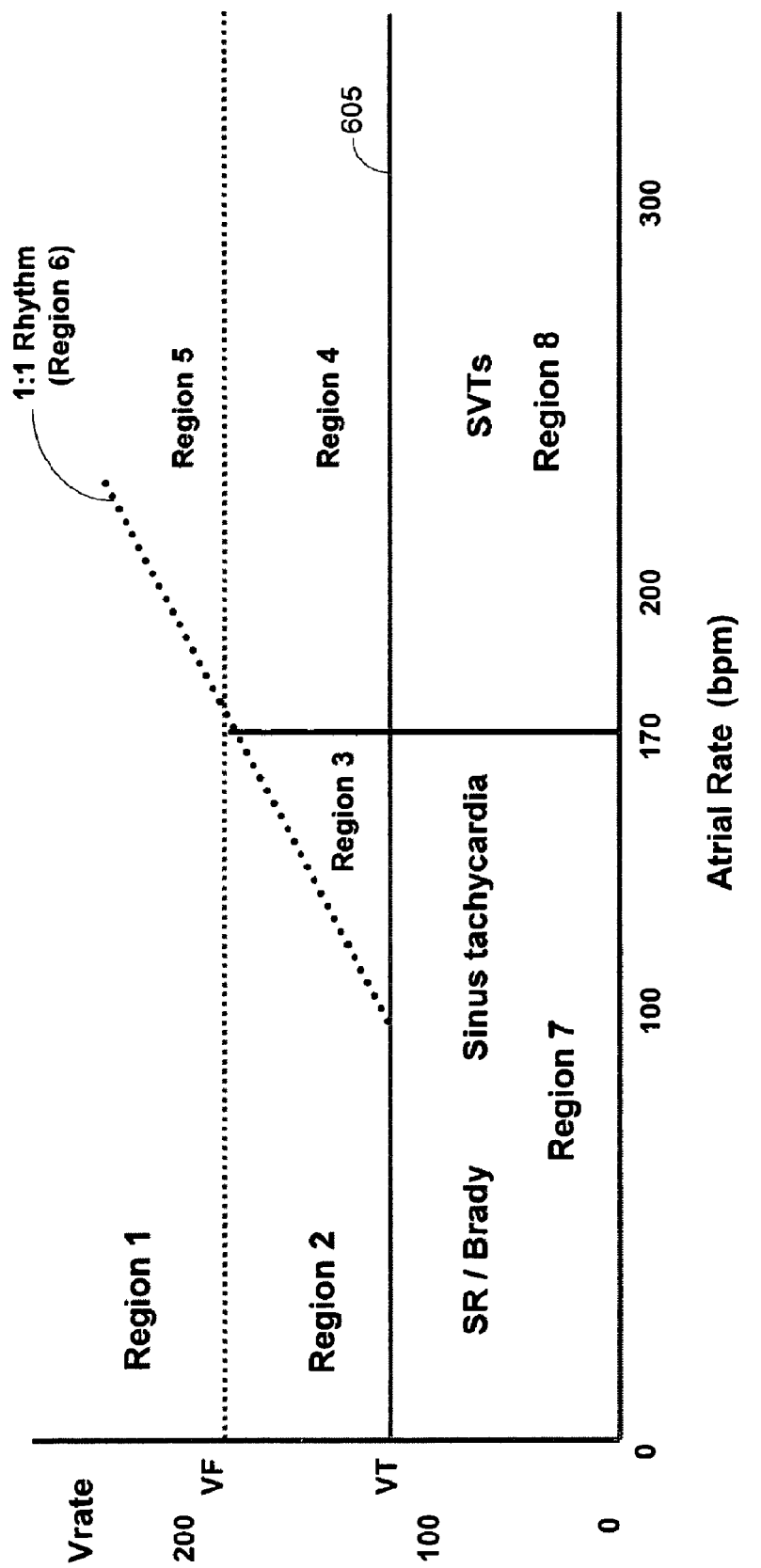
FIG. 6A is a graph illustrating regions of the A-V rate plane that may be utilized for classification of the cardiac rhythm in accordance with embodiments of the invention.

As previously described, the relationship between the atrial rate and the ventricular rate is particularly useful in discriminating between rhythms arising from the atria (SVT) and rhythms arising in the ventricles (VT). The relationship between the A-rate and the V-rate may be used as a starting point for classification purposes. FIG. 6A is a graph illustrating regions of the A-V rate plane that may be utilized for classification of the cardiac rhythm in accordance with embodiments of the invention.

In one embodiment, cardiac rhythms that fall into one or more areas of the A-V rate plane may be classified based on the relationship between the A rate and the V rate. If the V rate is less than a threshold value 605 and if the V rate is greater than the A rate (Region 7), then the rhythm may be classified as sinus rhythm or bradycardia. If the V rate is less than a threshold value 605 and if the A rate is greater than the V rate (Region 8), then the rhythm is classified as SVT. The system may be configured such that rhythms falling into Regions 7 and 8 may not initiate delivery of therapy. The flowcharts of FIGS. 6B, 7-11 illustrate methods of classifying a cardiac rhythm that falls into one of the Regions 1-6 in accordance with an embodiment of the invention.

Figure 6B:
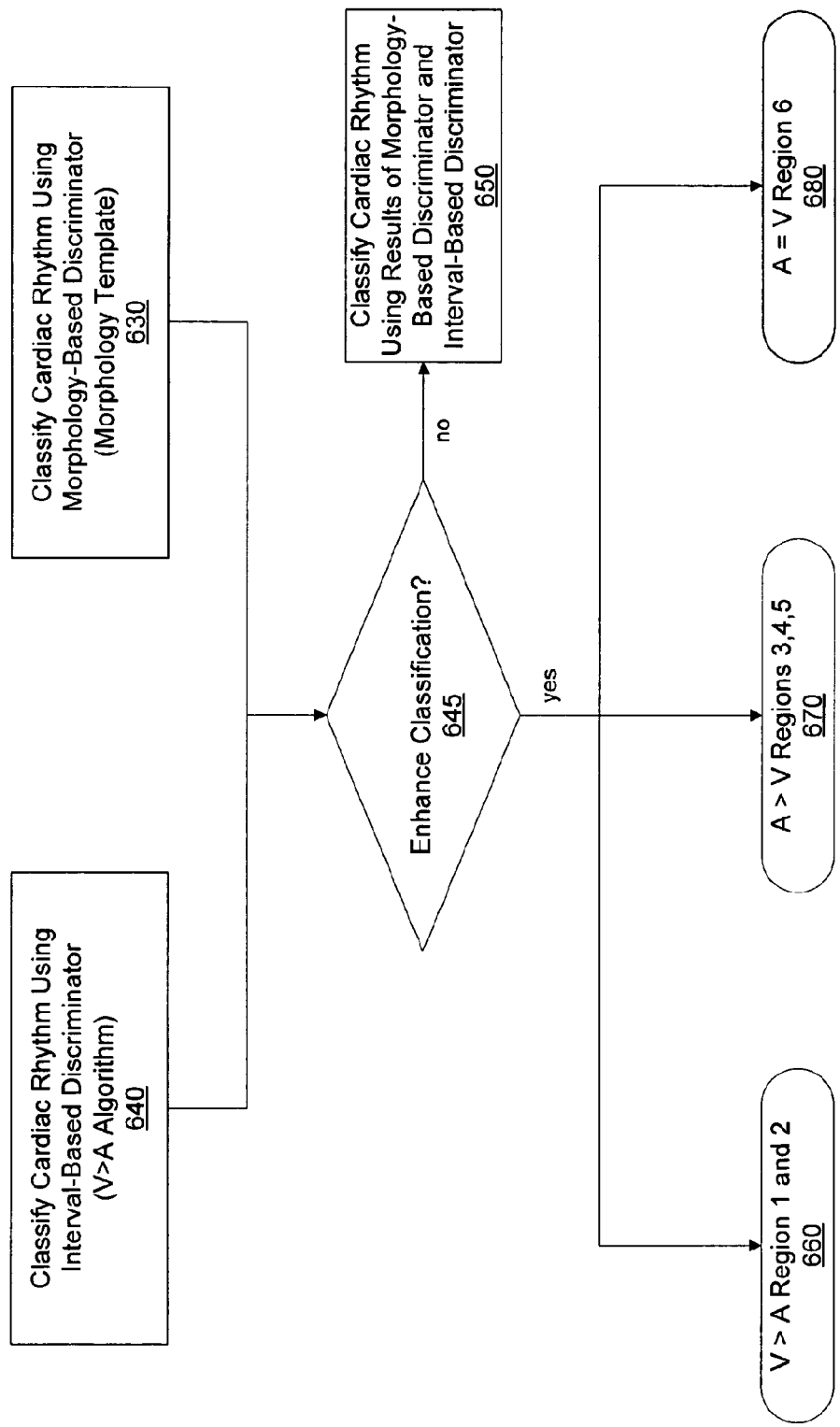
FIGS. 6B, 7, 8A, 9, 10, 11, and 12 are flowcharts illustrating a rhythm classification process utilizing at least one morphology-based rhythm discriminator and at least one interval-based rhythm discriminator in accordance with embodiments of the invention.

As illustrated in the flowchart of FIG. 6B, the cardiac rhythm is classified using a morphology-based rhythm discriminator 630 and an interval-based discriminator 640. For example, the morphology-based rhythm discriminator may involve comparing the cardiac beat signals to a morphology template representative of a supraventricular conducted rhythm (SVR) and determining the morphological similarity between the cardiac beat signal and the SVR template. If the cardiac signal is sufficiently similar to the SVR template, then the rhythm is classified as SVT. If the cardiac signal is not sufficiently similar to the SVR template, then the cardiac rhythm is classified as VT.

The interval-based discrimination procedure involves evaluating the relationship between the A-rate and the V-rate (V>A algorithm). If the V-rate is above a threshold value and the A-rate is sufficiently greater than the V rate, the rhythm is classified as SVT. If the V-rate is above the threshold value and the V-rate is sufficiently greater than the A-rate, then the rhythm is classified as VT. If the A rate and the V rate are about equal, then the result of the interval-based discriminator is indeterminate.

After classification of the rhythm using the morphology-based discriminator and the interval-based discriminator, the system determines whether or not to modify 645 the classification process to enhance rhythm classification. The system may determine that rhythm classification enhancement is not desired or required 650.

The system may determine to enhance rhythm classification, for example, if the results of the morphology- and interval-based rhythm discriminators conflict or are indeterminate. In these situations, the classification process may be modified and the rhythm re-classified using the modified classification process. If the system determines that enhancing the classification process is not required or desired, then the cardiac rhythm is classified based on the initial results of the morphology-based discriminator and/or the interval-based discriminator. The system may determine that enhancement of the classification process is not required or desired, for example, if the classification results produced by the morphology and interval-based discriminators are not in conflict and are not indeterminate.

Various optional methods 660, 670, 680 for modifying the classification process when the rhythm corresponds to various areas of the A-V plane are illustrated in the flowcharts of FIGS. 7-11 which follow from FIG. 6B. If the cardiac rhythm falls into 660 Regions 1-2 of the A-V rate plane, and the classification results of the morphology and interval-based discriminators conflict, then any or all of the optional process illustrated in the flowchart of FIG. 7 may be employed to resolve the conflict. The flowchart of FIG. 8 illustrates various optional processes that may be implemented if the cardiac rhythm falls into 670 Regions 3, 4, or 5 of the A-V rate plane. If the A rate and the V rate are about equal 680, then any or all of the optional processes illustrated in the flowcharts of FIG. 9, 10, or 11 may be used.

Figure 7:
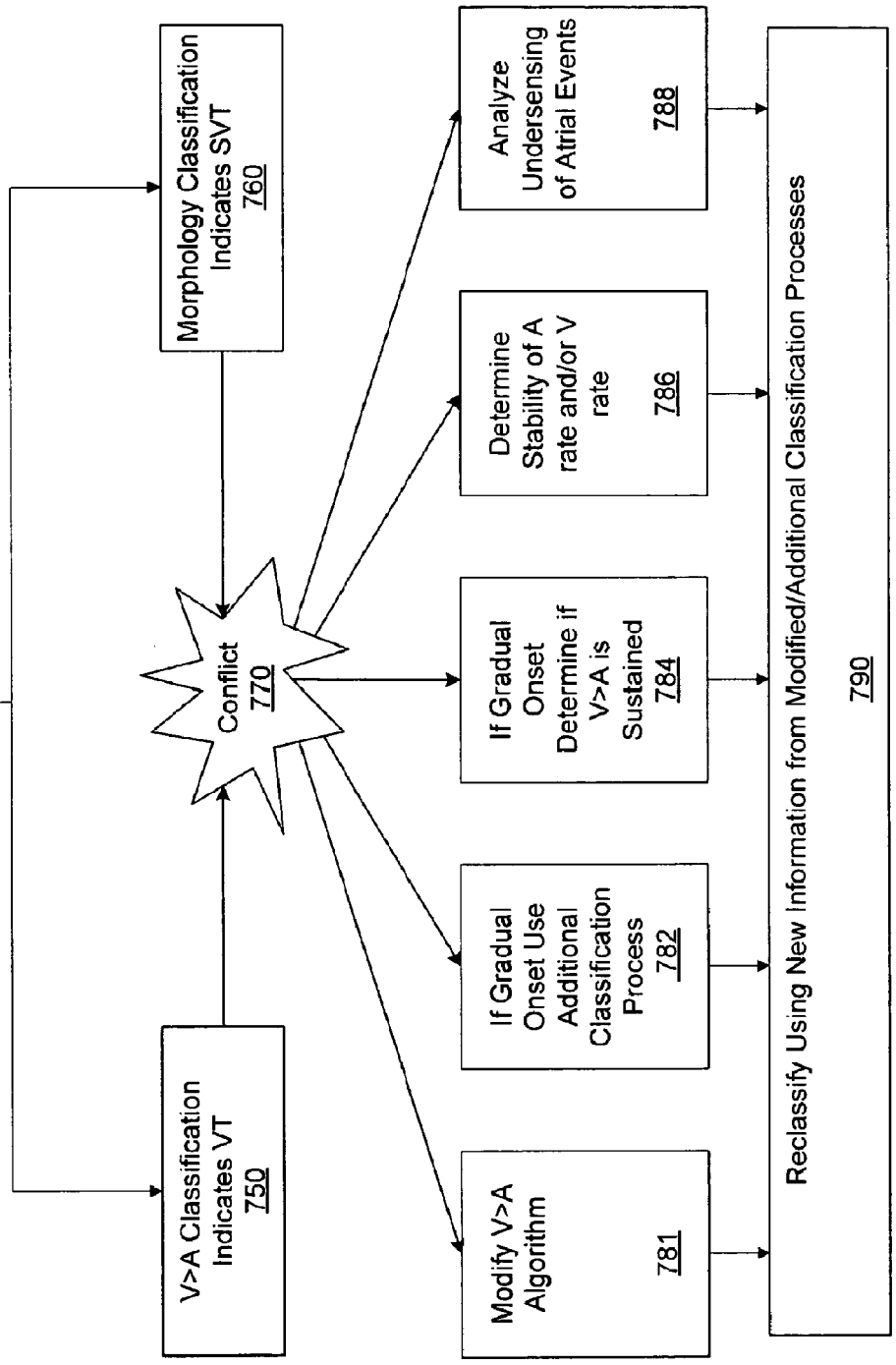

FIG. 7 illustrates various methods that may be employed to enhance cardiac rhythm classification when the cardiac rhythm falls into 710 Region 1 or Region 2 of the A-V rate plane. As previously discussed, the initial classification process, such as the process illustrated in FIG. 6B, may involve the use of an interval-based discriminator and a morphology-based discriminator. A cardiac rhythm that falls into Regions 1 or 2 may be initially classified 750 as VT by the interval-based rhythm discriminator because the ventricular rate is sufficiently greater than the atrial rate indicating a rhythm of ventricular origin. However, the morphology-based discriminator will indicate 760 SVT if the morphology of the cardiac signal is determined to be similar to an SVR template. In this scenario, a conflict 770 exists between the results of the interval-based rhythm discriminator and the morphology-based rhythm discriminator.

The conflict may be resolved by implementing one or more supplemental discrimination procedures that modify the initial classification process. Modification of the initial classification process may be accomplished by modifying 781 one or more parameters of the interval-based discriminator and/or the morphology-based discriminator, using additional discrimination procedures including evaluating rhythm onset and stability 782, 784, 786, and/or acquiring further information by analyzing 788 undersensing of atrial events. The processes for modifying the initial classification process 781, 782, 784, 786, 788 may be implemented in any order or may be implemented in parallel. In a preferred embodiment, modification of the V>A algorithm 781 is implemented first, with one or more additional processes 782, 784, 786, 788 optionally implemented if the rhythm remains unclassified. Following modification of the initial classification process by any of the procedures 781, 782, 784, 786, 788, the rhythm is reclassified 790 using the modified classification process.

If the results of the initial interval-based and morphology-based discriminators conflict, the initial interval-based discriminator (V>A algorithm) may be modified by changing one or more parameters of the algorithm. For example, the V>A algorithm may be modified by modifying the threshold for determination of VT. In one scenario, the initial algorithm may classify the rhythm as VT if the V-rate exceeds the A-rate by a predetermined threshold value, wherein the initial threshold value may be about 10 bpm. If the V-rate is substantially in excess of the A-rate, then the likelihood of VT is increased. The V>A algorithm may be modified by modifying the threshold value for detection of VT, such as by increasing the threshold to a higher value than was initially used, e.g. to about 50 beats. If the V-rate exceeds the A-rate by the new threshold value then the cardiac rhythm is reclassified as VT.

In another example of parameter modification 781, the intervals included in the A-rate and/or V-rate calculation may be modified and the relationship between the A-rate and the V-rate recalculated based on the modified intervals. In one embodiment, the A-rate calculation may be modified by changing the criteria for including A-A intervals used for the A rate calculation. The V-rate calculation may be modified by changing the criteria for including V-V intervals used for the V-rate calculation. For example, the V-rate calculation criteria may be modified by excluding one or more of the shortest V-V intervals out of a predetermined number of V-V intervals, e.g., excluding about 2 of the shortest V-V intervals out of about 10 intervals.

The A-rate calculation criteria may be modified by excluding one or more of the longest A-A intervals out of a predetermined number of A-A intervals, e.g., excluding about 2 of the longest A-A intervals out of about 10 intervals. The A-rate and/or V-rate is recalculated using the modified criteria and the relationship between the A-rate and the V-rate is determined. The system reclassifies 790 the cardiac rhythm based on the modified A-rate and/or V-rate parameters. Methods and systems for modifying the V>A algorithm, aspects of which may be utilized in the embodiments discussed herein, is described in commonly owned U.S. patent application Ser. No. 10/862,779, filed Jun. 7, 2004, and incorporated herein by reference.

If the results of the morphology and interval-based discriminators conflict 770, the conflict may be resolved using 782 additional discrimination procedures and/or additional information. For example if the morphology-based discriminator indicates SVT and the interval-based discriminator (V>A algorithm) indicates VT, the system may implement an additional discrimination procedure that checks the onset of the cardiac rhythm. If the onset is gradual, mitigating toward an SVT rhythm classification, information from other device processes may be used to confirm SVT. For example, sensor information used for adapting the pacing rate of a cardiac rhythm device may be used in the rhythm discrimination process.

Rate-adaptive pacemakers typically incorporate metabolic sensors to adapt the pacing rate to match the patient's hemodynamic need. A rate-adaptive pacing system may use an activity or respiration sensor to determine an appropriate pacing rate. Patient activity may be sensed, for example, using an accelerometer disposed within the housing of the pulse generator. Transthoracic impedance, which may be measured, for example, via intracardiac electrodes, may be used to determine respiration rate. Sensor information from the metabolic sensor is used to adjust the pacing rate to support the patient's hemodynamic need. If the sensors indicate the patient's activity and/or respiration rate is high, then the patient's pacing rate is increased to correspond to the level of activity or rate of respiration.

Sensor information from the pacing-rate adaptation process may be utilized in classifying a cardiac rhythm. For example, if the sensor output indicates relatively high patient activity or respiration rate, and the onset of the fast cardiac rhythm is gradual, then the system may reclassify 790 the rhythm as SVT.

Another example of using additional rhythm discriminators is provided at block 786. If the interval-based discriminator (V>A algorithm) indicates VT and the morphology-based discriminator indicates SVT, then an additional discrimination process may be implemented involving assessing the stability of the cardiac rhythm. A more stable ventricular rhythm is associated with VT, whereas a less stable rhythm is associated with SVT.

Stability analysis may be accomplished by measuring the degree of variability in the cardiac cycles, e.g., the V-V intervals between sensed R-waves. The degree of variability may allow the system to distinguish conducted atrial fibrillation (SVT), which may produce greater V-V variability, from monomorphic VT, which is typically stable. Stability analysis may also be used to differentiate monomorphic VT from polymorphic VT. Distinguishing monomorphic VT from polymorphic VT may be used in determining an appropriate treatment. For example, monomorphic VT may be treated using ATP, whereas polymorphic VT may be more successfully treated using defibrillation shocks.

The rhythm is reclassified 790 after assessing 786 the stability of the rhythm. If the rhythm is sufficiently stable, the system may reclassify the rhythm as VT.

Conflict between the interval-based and morphology-based discriminators 770 may be resolved using additional discrimination processes in addition to modification of an initially used discrimination process to further evaluate the cardiac rhythm. For example, as indicated at block 784, the system may utilize an additional discriminator (onset) and may modify a parameter (duration window size) of the V>A algorithm. The rhythm is reclassified 790 using the additional and modified discriminators.

If the onset of the rhythm is gradual, mitigating toward a classification of SVT, then the system may determine if the VT rhythm classification indicated by the V>A algorithm is sustained. Determining if the VT classification is sustained may be accomplished by reevaluating the relationship between the A rate and the V rate. The reevaluation may involve the same evaluation window size as was initially used, or an increased evaluation window size for measuring the A-A intervals and V-V intervals for determining the relationship between the A-rate and the V-rate.

For example, if the initially used window size is 10 intervals, the A-A and V-V intervals may be reassessed in a new window of 10 intervals. Alternatively, the window size for measuring the A-A and V-V intervals may be increased. In one implementation, the initially used window size may be about 10 intervals and the increased window size may be about 20 to about 40 intervals. The relationship between the A-rate and the V-rate is reevaluated using intervals measured during the new or modified window. The cardiac rhythm is reclassified 790 based on information from the onset discriminator and the V>A algorithm based on intervals measured during the new or modified evaluation window.

Another example of using additional information to resolve the conflict between discriminators involves determining 788 if atrial events are undersensed. Atrial events may be undersensed if the atrial rate is high causing atrial events to occur during a blanking period, e.g., a cross-chamber atrial blanking period following a sensed or paced ventricular event. Atrial events occurring during the blanking period are not sensed and thus are not included in the A rate estimation for the V>A algorithm. Undersensing of atrial events may be analyzed by reassessing atrial electrogram (EGM) data collected during the arrhythmic episode. The system may review the collected atrial data to determine if atrial events were present during the blanking period.

Analyzing the cardiac rhythm to find undersensed atrial events requires discriminating P-waves associated with intrinsic atrial depolarizations from far field R waves (FFRW). Far field R waves ventricular depolarizations sensed on the atrial channel. Far field R waves may be distinguished from legitimate P waves based on the relative peak values of the signal waveforms respectively associated with the two different types of waves. Legitimate P-waves have a different morphology than FFRWs and typically exhibit a larger peak amplitude than FFRWs.

In one implementation, the device may discriminate between legitimate P-waves and FFRW by comparing the peak amplitude of signals sensed during a blanking period to a value associated with FFRW. If the peak amplitude exceeds the threshold value, the signal is assumed to be a legitimate P-wave.

In another implementation, the device may form a template based on P-wave morphology. After formation of the P-wave template, sensed atrial signals are compared to the P-wave template, for example, by calculating a correlation coefficient using Equations 1 or 2. If the sensed atrial signals are similar to the P-wave template morphology, then the device determines that the sensed signals are legitimate P-waves. In another implementation, the device may form a FFRW template using signals sensed during a atrial blanking period following a ventricular event. If atrial signals sensed after formation of the FFRW template are similar to the template, then they are recognized as FFRWs. If the subsequently sensed signals are not similar to the template, then they are recognized as legitimate P-waves.

The use of a wide bandwidth amplifier may be helpful in discriminating legitimate P-waves from FFRWs. In devices that are equipped with a wide band amplifier and are capable of selecting electrode combinations for a particular channel, the atrial electrodes may be coupled to the wide band amplifier for detection of legitimate P-waves.

The newly uncovered P waves may be used in the A-rate estimation of the V>A algorithm. The cardiac rhythm is reclassified 790 based on the modified V>A algorithm which uses the uncovered P-waves.

The flowchart of FIG. 8 illustrates various optional procedures 882, 884, 885, 886, 888 that may be employed to enhance cardiac rhythm classification when the cardiac rhythm falls into 810 Regions 3, 4, or 5 of the A-V rate plane. As previously discussed, the initial classification process may involve the use of an interval-based discriminator and a morphology-based discriminator. A cardiac rhythm that falls into Regions 3, 4 or 5 may be initially classified 850 as SVT by the interval-based rhythm discriminator because the atrial rate is greater than the ventricular rate indicating a rhythm of atrial origin. However, the morphology-based discriminator will classify 860 the rhythm as VT if the morphology of the cardiac signal is not correlated to the SVR template. In this scenario, a conflict 870 exists between the results of the interval-based rhythm discriminator and the morphology-based rhythm discriminator.

The conflict 870 may be resolved by modifying the initial classification process. Modification of the initial classification process may be accomplished, for example, by modifying one or more parameters of the interval-based discriminator and/or the morphology-based discriminator and reclassifying the cardiac rhythm using the modified discriminators. Alternatively or additionally, one or more supplemental discrimination procedures may be used to classify the cardiac rhythm. Further, additional information from other cardiac processes may be used for determining the cardiac rhythm. Following modification of the initial classification process by any of the optional procedures 882, 884, 885, 886, 888, the rhythm is reclassified 890 using the modified classification process.

One example of the use of supplemental discriminators for classification of the cardiac rhythm is provided at block 882. If the interval-based discriminator (V>A algorithm) indicates SVT and the morphology-based discriminator indicates VT, then one or more supplemental discrimination processes may be implemented. The additional processes may involve, for example, assessing the stability of the cardiac rhythm, assessing the onset of the cardiac rhythm, assessing both the stability and the onset, or using other discrimination techniques as described below.

Rhythm stability evaluation may be useful in classifying cardiac rhythms because more stable ventricular rhythms are most often associated with monomorphic VT, whereas less stable rhythms are most often associated with AF. As previously discussed, stability analysis may be accomplished by measuring the degree of variability in the cardiac cycles, e.g., the V-V intervals between sensed R-waves.

As previously discussed, stability evaluation may be implemented, for example, by measuring the difference in intervals measured between ventricular events (V-V intervals). If the difference between the V-V intervals is less than a threshold value, then the rhythm may be determined to be stable. If the difference between the V-V intervals is greater than the threshold value, then the rhythm may be determined to be unstable. The degree of variability in V-V intervals may allow the system to distinguish conducted atrial tachyarrhythmia (SVT), which may produce greater V-V variability, from monomorphic VT, which typically exhibits a more stable ventricular rhythm.

The onset of the cardiac rhythm may additionally or alternatively be evaluated and used as a supplemental discriminator for classifying the cardiac rhythm. As previously discussed, onset criteria is useful in discriminating between sinus tachycardia and ventricular tachyarrhythmia. The onset parameter of the cardiac rhythm represents a measurement of how quickly the rhythm transitions from a slower rate to a faster rate. The onset of the rhythm may be examined to differentiate between physiologic sinus tachycardias, which typically begin slowly, from pathologic tachycardias, which typically begin suddenly. If the rate increase is gradual, the system may determine that a fast rhythm cardiac rhythm is sinus tachycardia and withhold therapy. However, if the rate abruptly increases, it is more likely that the rhythm is a pathologic rhythm and the system may deliver an appropriate therapy to terminate or mitigate the arrhythmia.

In an embodiment which exemplifies the use of 882 a supplemental discriminator along with a modification of the V>A discriminator, the system determines if the A-rate is greater than a threshold value. If so, the system may also evaluate the rhythm stability before reclassifying the rhythm. For example, if the A rate is greater than a threshold value, e.g. about 200 bpm, and the rhythm is unstable, then the system may classify the rhythm as SVT. After the rhythm is evaluated 882 using the supplemental discriminator and the modified V>A discriminator, the rhythm is reclassified 890.

In another embodiment, which exemplifies the use of multiple supplemental discriminators, the system may assess 888 both onset and stability discriminators. If the rhythm is stable and exhibits sudden onset, then the likelihood of atrial flutter (AFL) or atrial tachycardia (AT) is increased. The system may initiate procedures that discriminate potentially pace terminable atrial rhythms, such as AFL and AT from those that are more amenable to shock therapy, such as atrial fibrillation. Instead of comparing the A-rate to a threshold value, such as a threshold value associated with atrial fibrillation, the system may consider three elements, for example, a range statistic, a minimum interval and a dispersion statistic derived from a set of depolarization intervals. In one implementation, the range statistic comprises the difference between the largest and the smallest depolarization interval of the set, the minimum interval comprises the smallest interval, and the dispersion comprises the standard deviation of the intervals. The three elements may be compared to a threshold to identify a rhythm as atrial flutter or atrial fibrillation. Methods and systems for identifying rhythms, aspects of which may be incorporated into the embodiments described herein, are discussed in commonly owned U.S. Pat. No. 6,681,134 which is incorporated herein by reference. After the rhythm is evaluated 888 using the multiple supplemental discriminators, the rhythm is reclassified 890.

As previously described, conflict in the results of the interval-based discriminator and the morphology based discriminator may be resolved by modifying a parameter of one or both of the initial discriminators. An example of using a supplemental discriminator along with modifying a parameter of an initially used discriminator is illustrated at block 884. If the interval-based discriminator classifies the rhythm as SVT and the morphology-based discriminator classifies VT, then the correlation threshold for the morphology-based discriminator may be lowered 884. For example, the correlation coefficient may be lowered from about 0.94 to about 0.80. The rhythm may be reassessed using the modified correlation threshold. The stability of the rhythm may also be evaluated. After the rhythm is evaluated 884 based on stability and the modified correlation coefficient, the rhythm is reclassified 890.

Another example of using a modified initial discriminator is illustrated at Block 886. In this example, a different template may be used in place of the morphology discriminator template used in the initial classification. For example, the initial morphology template may represent morphology template associated with a resting state of the patient. The system may use a template associated with a different supraventricular rhythm. In one implementation, the system may substitute a template representative of bundle branch block (BBB) or a template that is representative of the patient's SVR during a period of increased activity or metabolic need.

The cardiac signal of one or more cardiac beats of the arrhythmic episode may be compared to the substituted template and a determination made as to whether a correlation exists between the rhythm and the template. In one example, the template used may be selected based on the activity level or metabolic need indicated by the system metabolic/activity sensor(s). The use of templates associated with various metabolic states of the patient may produce increased specificity in classifying the cardiac rhythm. Methods and systems for using multiple types of templates for classifying cardiac rhythms are described in commonly owned U.S. patent application Ser. No. 10/291,200 filed Nov. 8, 2002 and incorporated herein by reference. After the rhythm is evaluated 886 using the substituted template, the rhythm is reclassified 890.

Modification of the initial classification process may involve blending 885 the results of two or more initial or supplemental discriminators. In one example, the system may use the classification results of the morphology discriminator along with a rhythm stability discriminator. Marginally correlated rhythms may result in a higher weighting on stability. For example, if the correlation threshold for the morphology-based discriminator is about 0.9 to detect SVT, a marginally correlated rhythm may comprise a rhythm with a correlation factor of about 0.8. In this scenario, the system may evaluate the rhythm stability prior to reclassifying 890 the rhythm.

The conflict may be resolved by combining or blending 885 information from the initial rhythm discriminators, modified rhythm discriminators, and/or supplemental rhythm discriminators. Blending the information from the initial, modified, and/or supplemental discriminators may involve determining a weighting factor for each discriminator result. The cardiac rhythm is reclassified 890 based on a combination of the weighted results.

Blending 885 information from the initial, modified and/or supplemental rhythm discriminators may involve calculating a parameter of one rhythm discriminator as a linear or non-linear function of a parameter of another rhythm discriminator. In one embodiment, illustrated in the graph of FIG. 8B, a coefficient threshold used for morphology-based rhythm discrimination may be calculated as a linear function of the stability parameter. In other implementations, the stability parameter may be calculated based on the coefficient threshold.

The scenario involving computing one discrimination parameter as a function of another parameter provides a relatively simple example of blending rhythm discrimination processes. Another aspect of the invention involves blending discrimination parameters in a three dimensional or greater system. In one example, a particular discriminator parameter may be determined as function of any number of other discriminator parameters.

The processes 882, 884, 885, 886, 888 for modifying the initial classification process may be implemented in any order or may be implemented in parallel. In one implementation, the system may first examine the stability 882 of the A-rate and determine if the rate exceeds a threshold to identify the rhythm. Additional rhythm identification processes 884, 885, 886, 888 may be implemented if the rhythm cannot be identified from the A-rate stability and rate information.

In another implementation, a lower correlation threshold may be used 884 to determine if correlation with an SVR template is achieved using the lower correlation threshold. If the rhythm morphology is consistent with the SVR template using the lower correlation threshold, then the rhythm may be classified 890 as SVT. If the rhythm classification is still indeterminate, one or more rhythm identification processes 882, 885, 886, 888 may be employed.

In yet another implementation, the A-rate stability and rate may be checked 882, and the morphology may be evaluated using a lower correlation threshold 884. If neither of these processes yields a definitive rhythm identification, then the system may evaluate the morphology of the rhythm using a different type of template 886.

Blending information from rhythm discriminators may involve blending the results of the rhythm discriminators in multi-dimensional discrimination space to classify the rhythm. Methods for implementing blending results from discriminators are described in commonly owned U.S. Pat. No. 6,681,134.

Figure 9:
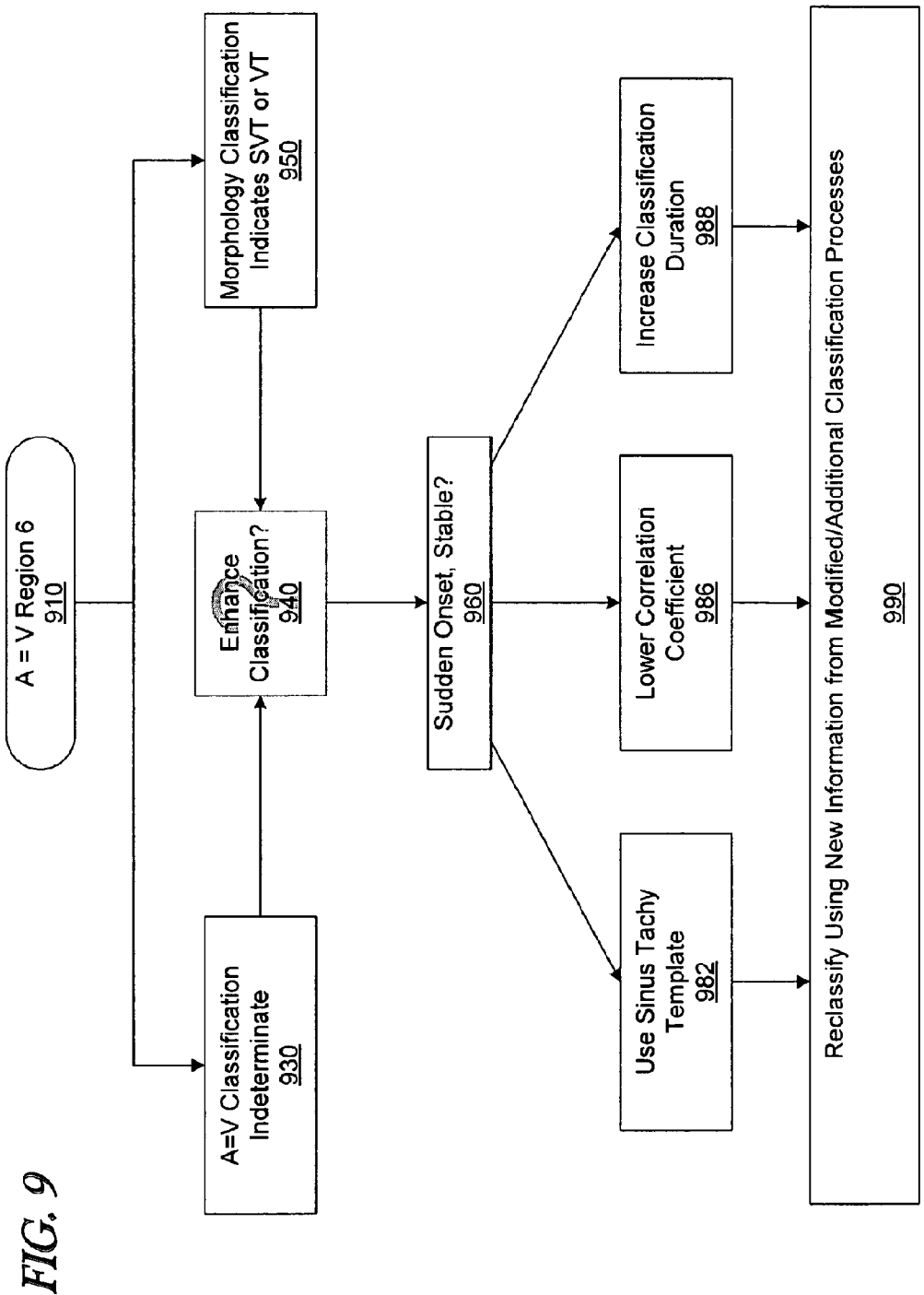
Figure 10:
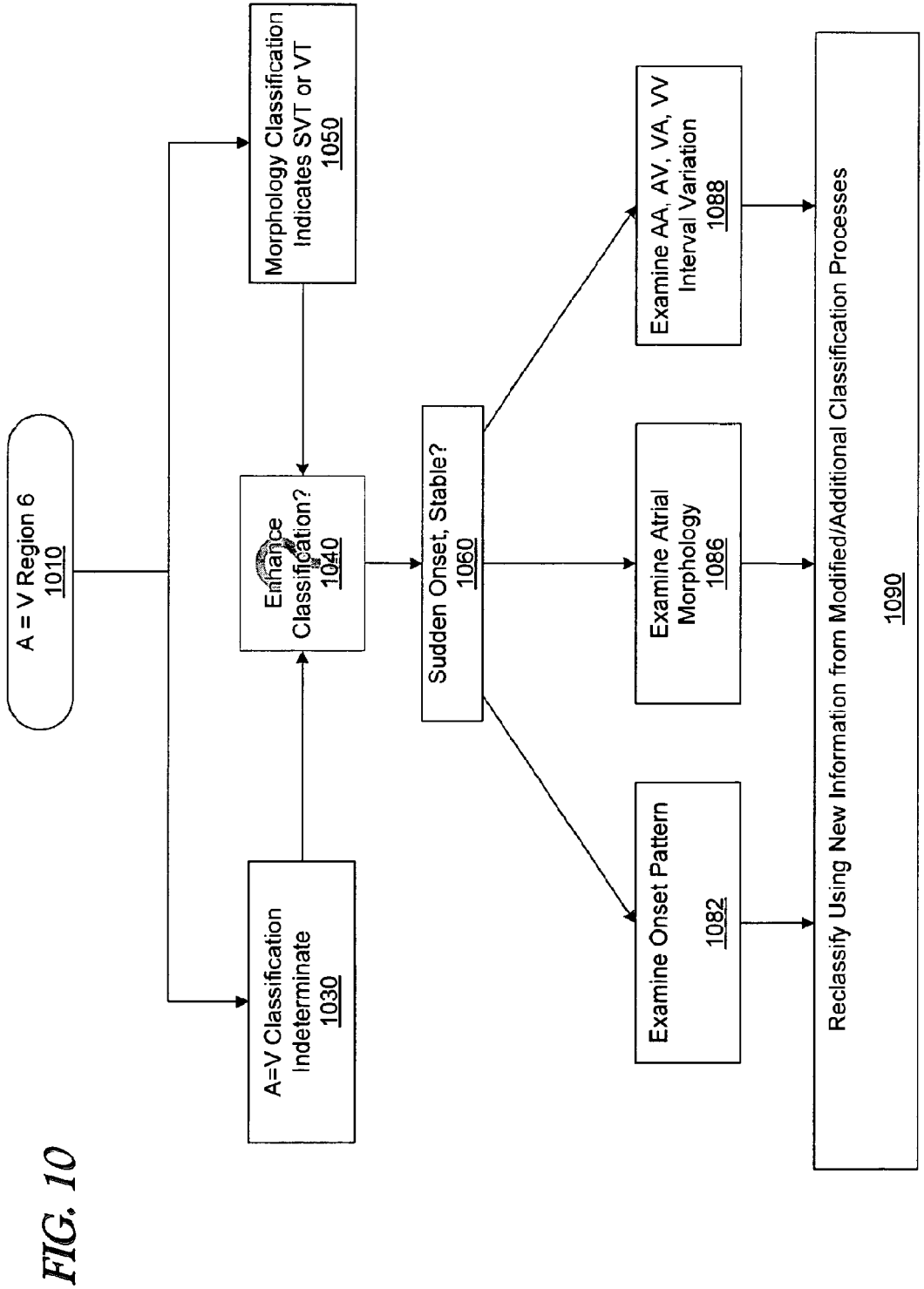
Figure 11:
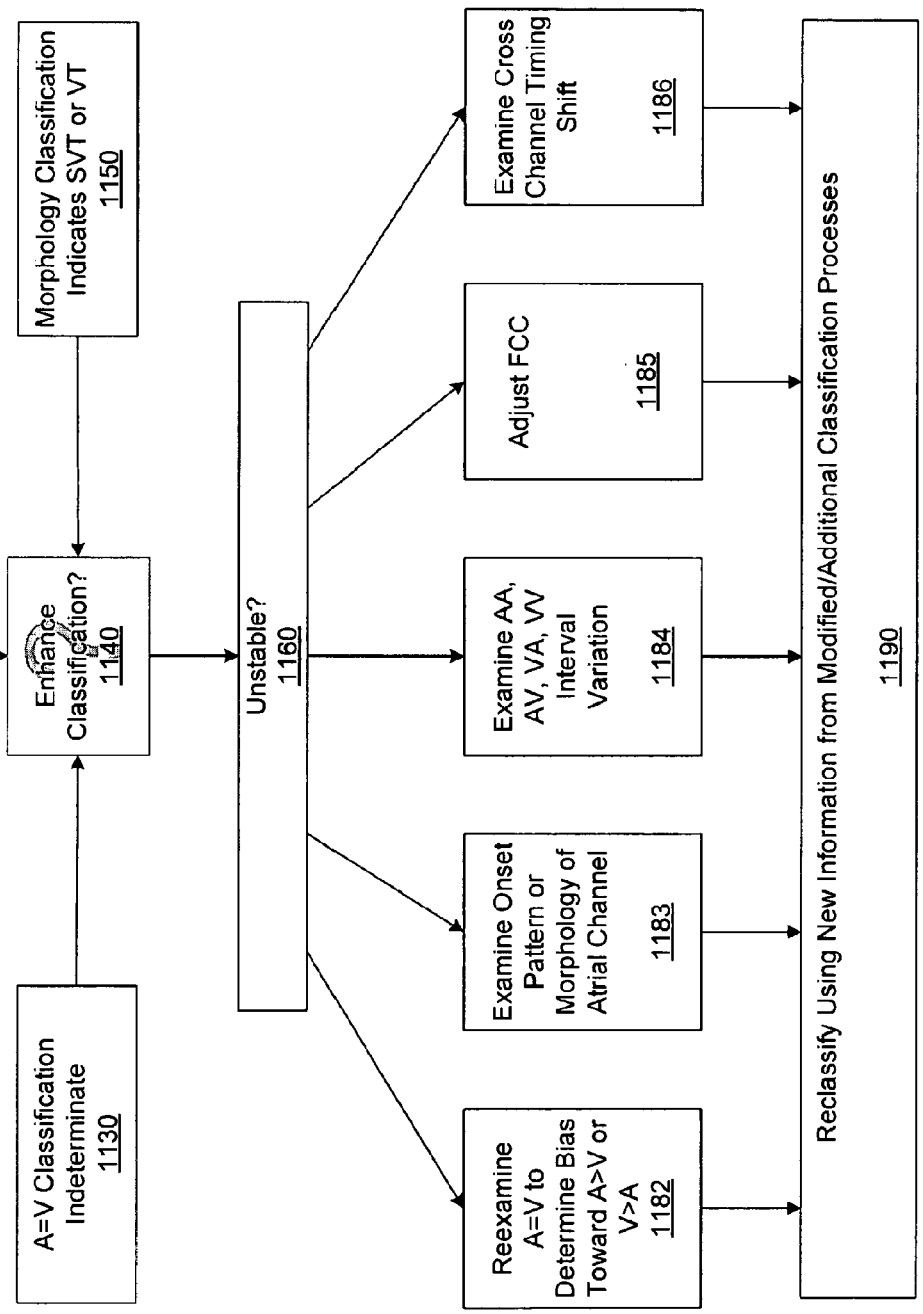

The flowcharts of FIG. 9-11 illustrate various procedures 960, 982, 986, 988, 1060, 1082, 1086, 1088, 1160, 1182, 1183, 1184, 1185, 1186 that may be employed to enhance cardiac rhythm classification when the A-rate and the V-rate are about equal 910, 1010, 1110. As in the embodiment previously discussed, the initial classification process may involve the use of an interval-based discriminator (V>A algorithm) and a morphology-based discriminator. A cardiac rhythm that falls into Regions 6 (A rate about equal to V rate) may be initially classified indeterminate by the interval-based rhythm discriminator. In this scenario, the interval-based discriminator cannot determine 930, 1030, 1130 the type of rhythm (classification is indeterminate). The morphology based discriminator may classify 950, 1050, 1150 the rhythm as SVT or VT. The rhythm classification may be enhanced 940, 1040, 1140 using one or more of the optional processes 960, 982, 986, 988, 1060, 1082, 1086, 1088, 1160, 1182, 1183, 1184, 1185, 1186. Following implementation of one or more of the optional processes 960, 982, 986, 988, 1060, 1082, 1086, 1088, 1160, 1182, 1183, 1184, 1185, 1186, the cardiac rhythm may be reclassified 990, 1090, 1190.

In the embodiments illustrated in FIGS. 9-11, the system use onset and stability discriminators to enhance the initial classification process. The flowchart of FIG. 9 illustrates optional processes 982, 986, 988 that may be employed for rhythm classification enhancement if the rhythm onset is gradual and the rhythm is stable 960. Preferably, one or both of processes 982 or 986 are implemented first with addition processes implemented if the rhythm is still unclassified. Following modification of the initial classification process by at least one of the optional procedures 982, 986, 988, the rhythm is reclassified 990 using the modified classification process.

The cardiac rhythm classification may be enhanced, for example, by modifying a parameter of one or both of the initial discriminators. For example, if the morphology-based discriminator classified the rhythm as VT during the initial classification, the correlation coefficient for the morphology-based discriminator may be lowered 986. In one implementation, the correlation coefficient is lowered from about 0.94 to about 0.8. The rhythm may be reassessed using the modified correlation coefficient. If the morphology of the cardiac beats of the rhythm are correlated to the SVR template using the decreased correlation coefficient, then the rhythm may be reclassified as SVT. If the morphology of the cardiac beats is uncorrelated to the SVR template, then the rhythm may be reclassified as VT.

Another example of modifying a parameter of an initial discriminator is illustrated at Block 982. In this example, a different template may be used in place of the morphology-based discriminator template used in the initial classification. In one scenario, the initial morphology template may represent morphology template associated with a resting state of the patient. The system may substitute a different template for classification, such as a template associated with a sinus tachycardia (ST) or other type of supraventricular rhythm. The ST template may be acquired during a sinus tachycardia episode, or may be generated based on a stored sinus tachycardia episode.

The cardiac signal may be compared to the substituted template and a determination made as to whether a correlation exists between the cardiac beats of the rhythm and the template. If the rhythm beats are correlated to the ST template, then the rhythm may be reclassified 990 as SVT.

Yet another example of modifying a parameter of an initial discriminator is illustrated at Block 988. In this example, the duration that the rhythm is evaluated may be increased to determine if the rhythm is a sustained rhythm.

In one implementation, the duration period that the rhythm is assessed may be increased to about 10 to about 20 seconds. The rhythm may be reclassified 990 using one or both of the initial rhythm discriminators based on information acquired during the increased duration period.

The flowchart of FIG. 10 illustrates optional processes 1082, 1086, 1088 that may be employed for rhythm classification if the rhythm onset is sudden and the rhythm is stable 1060. For example, process 1082 may be first applied followed by additional processes if required or desired. Following modification of the initial classification process by one or more of the optional procedures 1082, 1086, 1088, the rhythm is reclassified 1090 using the modified classification process.

Cardiac rhythm classification may be enhanced by examining 1082 the onset pattern 1082 and/or the timing or morphology 1086 of the atrial beats. In one implementation, classification of the cardiac rhythm may involve a set of rules based on onset pattern 1082 and atrial channel morphology 1086. One example of such a set of rules is that may be used for cardiac rhythm classification enhancement is as follows:

RULE 1. If the onset pattern is A1-V1-V2-A2 and the morphology or characteristics of A1 are different from the morphology or characteristics of A2 as detected on the atrial channel then the rhythm is likely to be VT. A rhythm that is correlated to the SVR template using the initial morphology-based discriminator may be further analyzed before classifying the rhythm as VT. In one embodiment, AA, AV, VA, and/or VV interval analysis is implemented to confirm the rhythm is VT.

RULE 2. If the onset pattern is A1-V1-A2-V2 and the morphology or characteristics of A1 and A2 are unchanged as detected on the atrial channel, then a rhythm that is uncorrelated to the SVR template using the initial morphology-based discriminator but correlated using a lowered FCC threshold or secondary template is classified as SVT.

RULE 3. If the onset pattern is A1-V1-A2-V2 or A1-A2-V1-A3-V2 and the morphology or characteristics of the atrial beats A1, A2, A3 change from beat to beat as detected on the atrial channel, then a rhythm that is uncorrelated to the SVR template using the initial morphology-based discriminator but correlated using a lowered FCC or secondary template is classified as SVT.

The above rules represent one possible set of rules that may be utilized in connection with classifying the cardiac rhythm. Other or additional rules may alternatively be used. For example, the rules may be based only on onset pattern or only on atrial morphology.

Cardiac rhythm classification may be enhanced by examining 1088 the variation of various intervals, including A-A intervals A-V intervals, V-A intervals and/or V-V intervals. SVT and VT rhythms may be identified based upon the relative variability of the VA and AV intervals. For example, if the atrial rate is about equal to the ventricular rate, an SVT may be detected if the VA interval variability exceeds the AV interval variability. A VT may be detected if the AV interval variability exceeds the VA interval variability. Methods and systems for identifying cardiac rhythms based on evaluating pairing of atrial and ventricular intervals and/or interval variability, aspects of which may be utilized in the embodiments described herein, are discussed in commonly owned U.S. Pat. No. 6,522,917 and U.S. patent application Ser. No. 09/982,116, filed Oct. 17, 2001, which are incorporated herein by reference.

The flowchart of FIG. 11 illustrates optional processes 1182, 1183, 1184, 1185, 1186 that may be employed for rhythm classification enhancement. The optional processes 1182, 1183, 1184, 1185, 1186 of FIG. 11 may be utilized if the A-rate is about equal to the V-rate 1110, the results of the V>A discriminator are indeterminate 1130, the rhythm is classified 1150 by the morphology discriminator as VT or SVT, and the rhythm is unstable 1160. If the A-rate is about equal to the V-rate 1110, the rhythm is unstable and uncorrelated to the SVR template, there is a possibility that the rhythm is SVT. The processes 1182, 1183, 1184, 1185, 1186 may be used to enhance 1140 the discrimination between VT and SVT rhythms. Following modification of the initial classification process by any of the optional procedures 1182, 1183, 1184, 1185, 1186, the rhythm is reclassified 1190 using the modified classification process.

Cardiac rhythm classification may be accomplished 1183 using a set of rules involving the onset pattern and the characteristics or morphology as previously described in connection with block 1082 of FIG. 10 above. Alternatively or additionally, the rhythm classification may involve determining 1184 interval variations as described previously in connection with block 1088.

The correlation coefficient may be modified 1185 as described in connection with 884 of FIG. 8. For example, the feature correlation coefficient calculated using Equation 1 may be decreased from about 0.94 to about 0.8. If the rhythm morphology is correlated to the template using the decreased correlation coefficient, then the rhythm may be reclassified 1190 as SVT.

In one example, the factors used in the V>A algorithm, e.g., the A-rate and/or V-rate may be modified 1182 to determine if the A-rate and V-rate are biased toward A>V or V>A. In one implementation, the A-rate and/or V-rate may be redetermined using a new criteria for including beats in the A-rate and/or V-rate calculation. As previously described in connection with block 781 of FIG. 7, the intervals included in the A-rate and/or V-rate calculation may be modified and the relationship between the A rate and the V rate recalculated using the new estimations. In one embodiment, the A rate estimation may be modified by changing the criteria for including A-A intervals used for the A rate calculation. The V-rate estimation may be modified by changing the criteria for including V-V intervals used for the V rate calculation. For example, the V rate estimation criteria may be modified by excluding one or more of the shortest V-V intervals out of a predetermined number of V-V intervals, e.g., excluding about 2 of the shortest V-V intervals out of about 10 intervals.

The A-rate calculation criteria may be modified by excluding one or more of the longest A-A intervals out of a predetermined number of A-A intervals, e.g., excluding about 2 of the longest A-A intervals out of about 10 intervals. The A-rate and/or V-rate is recalculated using the modified criteria and the relationship between the A-rate and the V-rate is determined. The cardiac rhythm is reclassified 1190 based on the modified A-rate and/or V-rate parameters.

In one implementation, the A=V algorithm is reevaluated to determine bias toward A>V or V>A. After the reevaluation, if A>V, then the FCC may be lowered 1185 and the morphology classified based on the lowered FCC.

The discrimination procedures illustrated by blocks 1182, 1183, 1184, and 1185 above may be used in combination with examining cross chamber timing shift 1186 of the rate and shock channel electrograms. The timing shift between the ventricular rate channel and the ventricular shock channel may be evaluated to determine if the shock channel signal has shifted with respect to the rate channel signal. For example, the timing shift of feature points of the shock channel may be checked, such as by checking the timing difference between the rate channel fiducial point and the peak of the shock EGM. If the timing difference is changed more than about 1 sample point from that of the template, then the shock channel is time-shifted with respect to the rate channel. For example, the timing shift may be in the range of about 5 to about 15 ms in either direction. The correlation coefficient is calculated using the time-shifted shock channel.

After a rhythm has been classified, the rhythm may transition from one type of rhythm to another type of rhythm. For example, a rhythm previously classified as SVT may transition from SVT to VT or another type of SVT. Identification of rhythm transitions may be desirable to allow the system to deliver an appropriate therapy for rhythms that are responsive to therapy. Rhythm transitions may be identified using a rules-based methodology. In some implementations, it is desirable to structure the rules so that there is a certain amount of delay or hysteresis in performing the rhythm identification. This hysteresis in the rhythm identification process helps to avoid oscillations back and forth between two or more rhythm identification decisions. As with the initial rhythm identification processes described above, rhythm transitions may be identified using multiple rhythm discriminators. When more than one independent rhythm discriminator is used, one rhythm discriminator may detect a rhythm transition, while another rhythm discriminator does not detect a change. If the results of the rhythm discriminators conflict with regard to rhythm transition, the system may implement one or more procedures to resolve the conflict.

In one example of rhythm transition, the rhythm determined by the interval-based discriminators (V-rate, V>A algorithm, rhythm onset, rhythm stability) is unchanged but the morphology of the rhythm changes. For example, if a morphology template is used, the rhythm which was previously correlated to the template becomes uncorrelated. When a correlated rhythm is suddenly uncorrelated, if the interval-based rhythm decision is consistent, the rhythm is possibly not changed. However, if the rate is suddenly changed and stable or V>A, the rhythm is changed to VT. Another possibility is that an SVT rhythm is changed to a different type of SVT.

may be evaluated using a lower correlation threshold or by examining the cross chamber timing shift of the rate and shock channel electrograms as described herein. If the rhythm is correlated to the SVR template using the lower correlation threshold or using the timing shift, then the rhythm remains SVT. However, if the rate is accelerated, then a rhythm transition from SVT to VT may have occurred.

Rule 4: If an SVT rhythm that was previously A>V or A=V becomes uncorrelated, and becomes or remains A=V and is unstable, then any combination of the discrimination processes 1182, 1183, 1184, 1185, 1186 outlined in FIG. 11 may be used to determine if a rhythm transition has occurred.

The rules discussed above illustrate a rules-based methodology that may be used to identify rhythm transitions in accordance with embodiments of the invention. Another example of a rules based methodology for identifying rhythm transitions is illustrated by Table 1 and the rules that follow.

Table 1 illustrates possible output states of interval-based discriminators for a number of example cases that will be used to illustrate a rules-based methodology for detecting or confirming rhythm transitions.

TABLE 1

| | Case | | | | | | | |
|---|---|---|---|---|---|---|---|---|
| | 1 | 2 | 3 | 4 | 5 | 6 | 7 | 8 |
| V > A Algorithm | A > V | A > V | A > V | A > V | A = V | A = V | A = V | A = V |
| Sudden Onset | True | True | False | False | True | True | False | False |
| V rate Stable | True | False | True | False | True | False | True | False |

Figure 12:
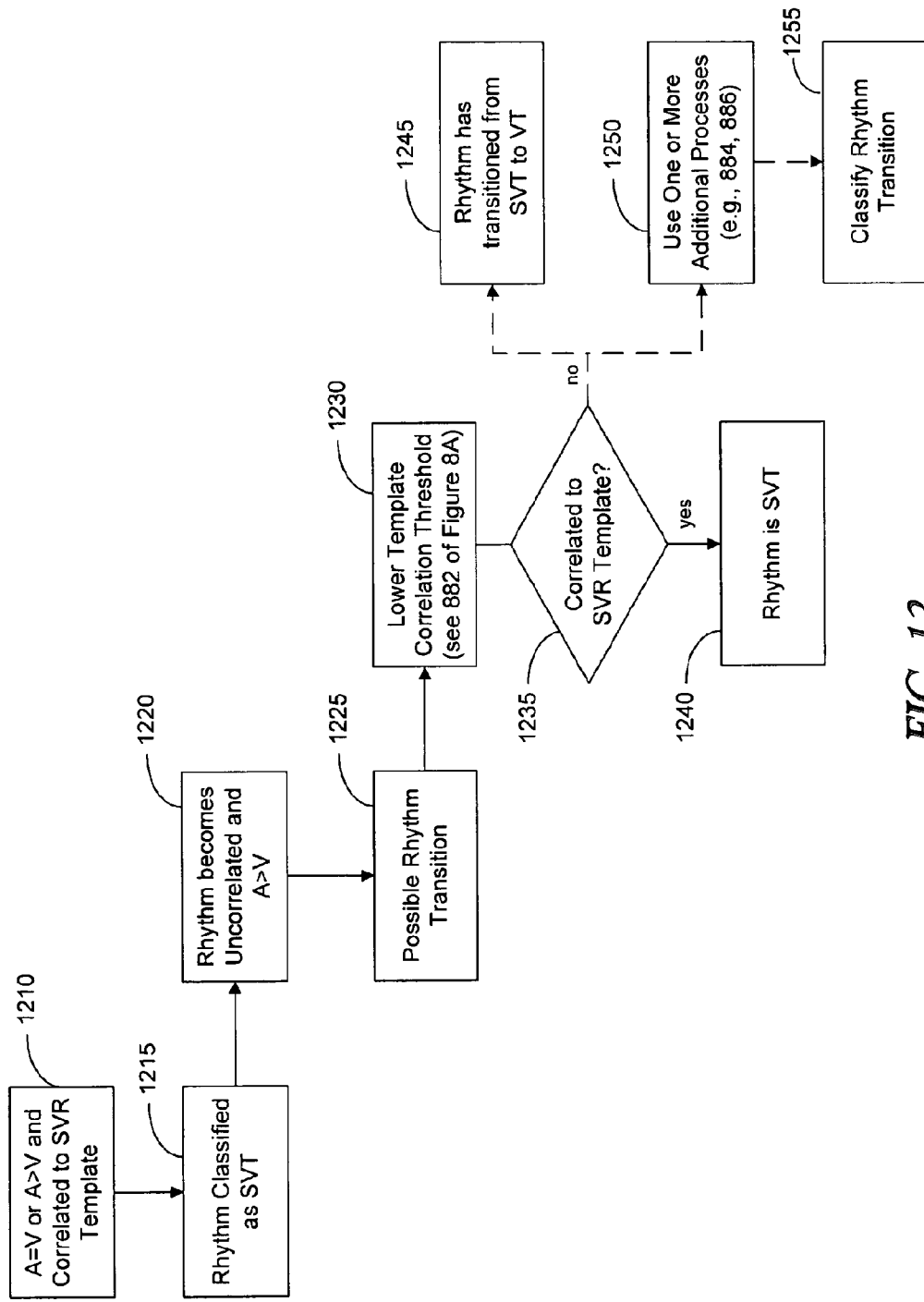

In one embodiment, the following set of rules may be implemented to identify rhythm transitions from SVT to VT:

Rule 1: If an SVT rhythm that was previously A=V or A>V and correlated to the SVR template changes to uncorrelated and becomes or remains A>V, then the processes described in connection with FIG. 8A may be used to reassess the rhythm. This rhythm transition rule is illustrated by blocks 1220-1255 of FIG. 12. An A=V or A>V rhythm that is correlated 1210 to the SVR template is classified 1215 as SVT. This rhythm becomes 1220 uncorrelated to the SVR template and becomes or remains A>V. The system determines 1225 if a rhythm transition has occurred. As described in connection with block 882 of FIG. 8A, the template correlation threshold may be lowered 1230 and the morphology of the rhythm compared to the SVR template using the lower correlation threshold. If the rhythm is correlated 1235 to the SVR template using the lower correlation threshold, then no transition has occurred and the rhythm remains 1240 SVT.

In one optional implementation, if the rhythm is not correlated 1235 to the SVR template using the lower correlation threshold, then the system determines that a rhythm transition has occurred 1245 and the rhythm is reclassified as VT.

Figure 8A:
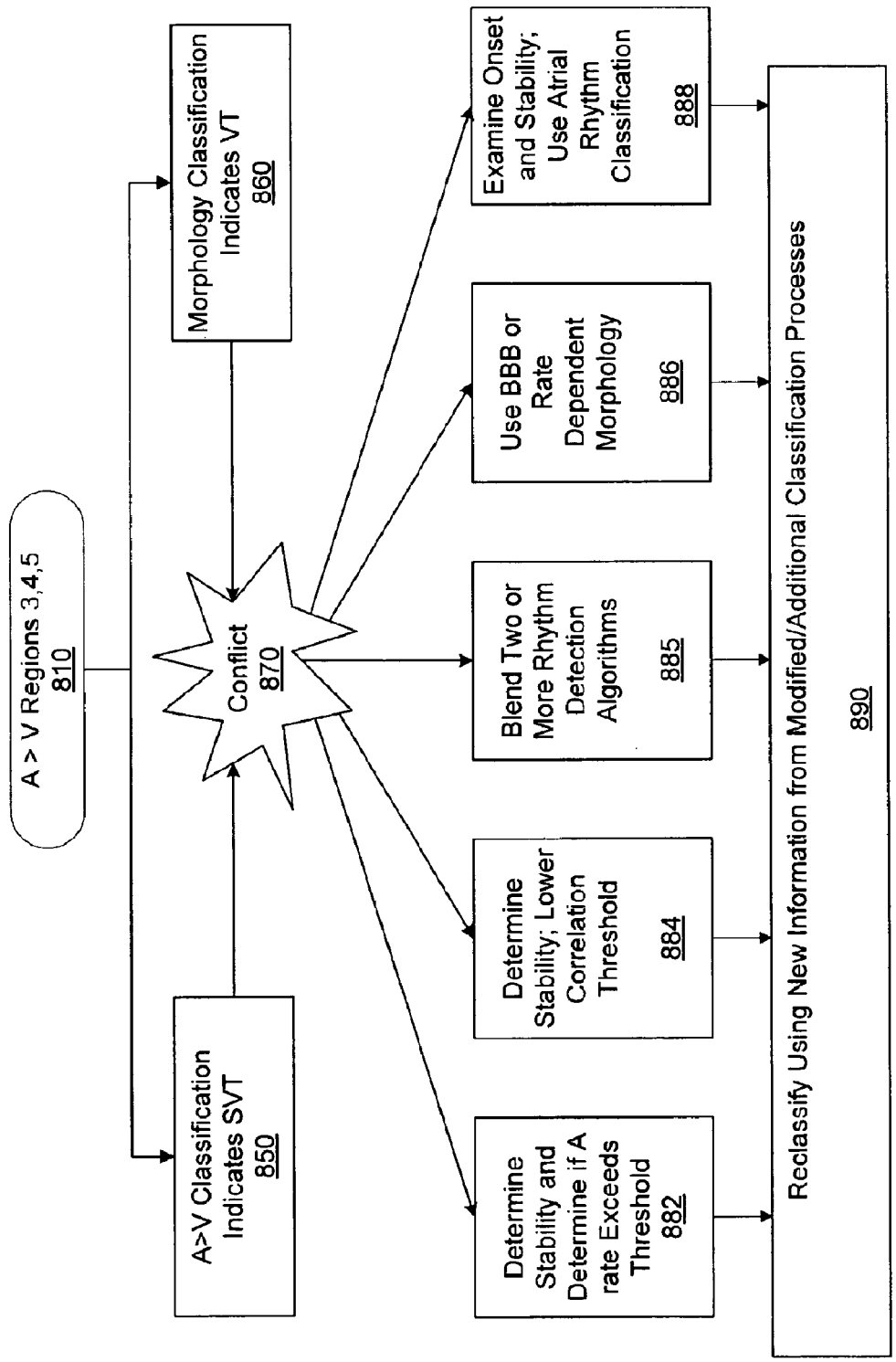
Figure 8B:
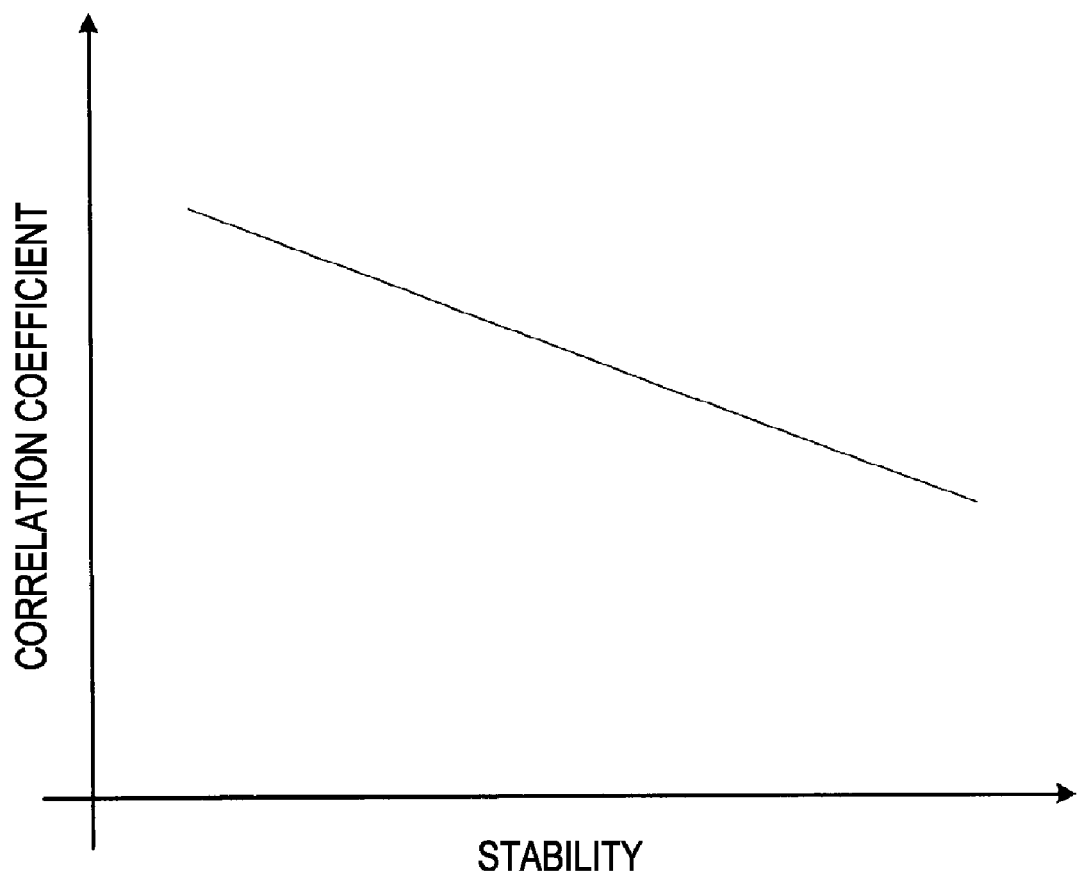
FIG. 8B is a graph illustrating modification of a correlation coefficient used for morphology-based rhythm discrimination in accordance with embodiments of the invention.

In another optional implementation, if the rhythm is not correlated 1235 to the SVR template using the lower correlation threshold, then addition rhythm identification processes, such as those described in connection with blocks 884, 885, 886, and 888 of FIG. 8A may be employed 1250. The rhythm is reassessed 1255 using information acquired from the additional rhythm identification processes.

Rule 2: If an SVT rhythm that was previously A>V becomes A=V and uncorrelated and is stable, then the processes 982, 986, 988, 1082, 1086, 1088 described in connection with FIG. 9 or 10 may be used to identify the rhythm.

Rule 3: If an SVT rhythm that was previously A=V stays A=V but becomes uncorrelated and is stable, then the rhythm Case 1 and 3: A>V and a Correlated and Stable Rhythm is Suddenly Uncorrelated.

In each case listed in Table 1, the rhythm is correlated to the SVR template and initially classified as SVT. For example, Case 1 identifies a rhythm that was initially classified as SVT, with morphology correlated to the SVR template, A>V, sudden onset, and stable V-rate. Case 2 identifies a rhythm that was initially classified as SVT, with morphology correlated to the SVR template, A>V, without sudden onset, and stable V-rate.

For cases 1 and 3, the following rules may be applied to determine if a rhythm shift has occurred when A>V and a correlated and stable rhythm is suddenly uncorrelated:

Rule 1: If the AV pattern and V rate are consistent, the type of rhythm is not changed. The possible reasons for non-correlation to the SVR template are morphological change or the cross chamber timing shift of the rhythm (rate channel vs. shock channel signal shift) during sustaining SVT at high heart rate. One or more processes for confirming that the rhythm remains unchanged may be implemented. For example, the timing shift of feature points of the shock channel may be checked, such as by checking the timing difference between the rate channel fiducial point and the peak of the shock EGM. If the timing difference is changed more than about 5 ms from that of the template, then the shock channel is shifted with respect to the rate channel and the correlation coefficient is calculated. If the rhythm is correlated with the extended shift, then the system confirms that it the rhythm is correlated to the SVR template.

Alternatively, a high rate SVR template or a second SVR template can be used and the correlation coefficient calculated. If the rhythm is correlated to the high rate SVR template, this indicates that there is no change in the rhythm. Further, confirmation that the rhythm is unchanged may be implemented by easing conditions of correlation such as by lowering the correlation coefficient threshold or the number of correlated beats in a window for SVT.

Rule 2: When the rhythm becomes morphologically uncorrelated to the SVR template, and if the rate is suddenly changed and a previously stable rhythm becomes unstable, then the rhythm is most likely changed from a stable SVT to an unstable SVT. The morphological variation or CCT shift may be checked to confirm the rhythm change from stable to unstable SVT.

Case 2 and 4: A>V. Correlated and Unstable Rhythm is Suddenly Uncorrelated.

Rule 1: If the AV pattern and V rate are unchanged, the type of rhythm is most likely not changed. One or more processes for confirming that the rhythm remains unchanged may be implemented by calculating the correlation coefficient using a different template or using extended shift as described above.

Case 5 and 7: A=V. Correlated and Stable Rhythm is Suddenly Uncorrelated.

Rule 1: If the AV pattern and V rate are unchanged, the type of rhythm is not changed. Confirmation may be implemented by calculating the correlation coefficient using a different template or using extended shift as described above.

Rule 2: When the rhythm becomes suddenly uncorrelated, and if the rate suddenly changes and becomes unstable, then the rhythm is changed from a stable SVT to an unstable SVT or VT. Confirmation of the rhythm change may be implemented by calculating the correlation coefficient using a different template or using extended shift as described above.

Case 6 and 8: A=V, Correlated and Unstable Rhythm is Suddenly Uncorrelated.

Rule 1: If the AV pattern and V rate are unchanged, the type of rhythm is most likely not changed. Confirmation may be implemented by calculating the correlation coefficient using a different template or using extended shift as described above.

Rule 2: If the rhythm becomes uncorrelated and if the V rate was suddenly changed and is unstable, and A>V, then the rhythm has transitioned to AF. Confirmation may be implemented by calculating the correlation coefficient using a different template or using extended shift as described above.

In another example of rhythm transition, the rhythm determined by a morphology-based discriminator is unchanged but the classification determined by an interval-based discriminator changes. A rules-based methodology may be implemented for detecting or confirming rhythm transitions when the rhythm classification of the morphology-based discriminator is unchanged, but the rhythm classification of the interval-based discriminator changes from SVT to VT. Rules 1 and 2 illustrated below provide yet another example of a rules-based methodology for determining rhythm transitions in accordance with embodiments of the invention.

Rule 1: If A>V or A=V is changed to V>A while the rhythm is correlated to the SVR template, the transition from SVT to VT may be confirmed by the stability of V>A or another independent algorithm.

Rule 2: If A>V or A=V is unchanged while the V rate or the stability is suddenly changed, the rhythm has possibly changed from one type of SVT to another type of SVT.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for classifying a tachyarrhythmia in a heart, the method comprising:
   sensing, at a patient device, one or more sequences of atrial and ventricular contractions associated with the tachyarrhythmia;
   selecting, at the patient device, one or more patterns that represent an onset pattern, the patterns including respective sequences of atrial and ventricular contractions; and
   obtaining, at the patient device, a first classification of the tachyarrhythmia based on whether a match exists between the one or more sequences of atrial and ventricular contractions and the one or more patterns.

2. The method in claim 1, comprising:
   detecting whether the tachyarrhythmia is sudden onset;
   determining whether an atrial rate is approximately equal to a ventricular rate; and
   if the tachyarrhythmia is sudden onset and the atrial rate is approximately equal to the ventricular rate, then classifying the tachyarrhythmia using whether the match exists.

3. The method of claim 1, wherein the obtaining the first classification comprises:
   identifying a sequence of atrial and ventricular contractions associated with the tachyarrhythmia; and
   classifying the sequence as more likely indicative of ventricular tachyarrhythmia if two or more ventricular contractions occur between consecutive atrial contractions within the sequence.

4. The method of claim 1, wherein the obtaining the first classification comprises:
   identifying a sequence of atrial and ventricular contractions associated with the tachyarrhythmia; and
   classifying the sequence as more likely indicative of supraventricular tachyarrhythmia if two or more atrial contractions occur between consecutive ventricular contractions within the sequence.

5. The method of claim 1, wherein the obtaining the first classification comprises:
   identifying a sequence of atrial and ventricular contractions associated with the tachyarrhythmia; and
   classifying the sequence as more likely indicative of ventricular tachyarrhythmia if two or more consecutive ventricular contractions occur between consecutive atrial contractions without having two or more consecutive atrial contractions occur between consecutive ventricular contractions within the sequence.

6. The method of claim 1, comprising:
   establishing a matching threshold value using a result of the first classification; and
   performing a comparison using the established matching threshold value to obtain a second classification of the tachyarrhythmia.

7. The method of claim 6, wherein the comparison is a morphology analysis.

8. The method of claim 6, comprising:
   determining whether a therapy is necessary;
   choosing a therapy using the second classification if a therapy is deemed necessary; and
   delivering the therapy.

9. The method of claim 6, wherein the establishing the matching threshold comprises at least one of:
   raising or maintaining the matching threshold if the first classification is ventricular tachycardia; and
   lowering or maintaining the matching threshold if the first classification is supraventricular tachycardia.

10. A tachyarrhythmia detection and classification system, comprising:
- a sensing circuit, adapted to sense at least one cardiac signal; and
- a control system, coupled to the sensing circuit, the control system including:
  - an arrhythmia classification processor adapted to detect a tachyarrhythmia based on a heart rate obtained from the at least one cardiac signal; and
  - an rhythm discriminator adapted to obtain a first classification of a tachyarrhythmia as either ventricular tachycardia (VT) or supraventricular tachycardia (SVT) based on whether one or more patterns exists in a sequence of atrial and ventricular depolarizations detected by the arrhythmia detection module, the one or more patterns representing an onset pattern, and the patterns including respective sequences of atrial and ventricular contractions.

11. The system of claim 10, wherein the rhythm discriminator is adapted to detect a sudden onset of a tachyarrhythmia.

12. The system of claim 10, wherein the rhythm discriminator is adapted to detect when the atrial rate is substantially equal to a ventricular rate.

13. The system of claim 10, wherein the rhythm discriminator module is adapted to:
- access a memory for representing a sequence of atrial or ventricular contractions;
- access a pattern of two or more ventricular contractions occurring between consecutive atrial contractions; and
- classify the sequence as more likely indicative of ventricular tachycardia if the pattern is found in the sequence.

14. The system of claim 10, wherein the rhythm discriminator module is adapted to:
- access a memory for representing a sequence of atrial or ventricular contractions;
- access a pattern of two or more atrial contractions occurring between consecutive ventricular contractions; and
- classify the sequence as more likely indicative of supraventricular tachycardia if the pattern is found in the sequence.

15. The system of claim 10, wherein the rhythm discriminator module is adapted to:
- access a matching threshold value that is established based on the first classification; and
- compare a morphology of one or more beats under examination to a template morphology using the established matching threshold value to obtain a second classification of the tachyarrhythmia.

16. The system of claim 15, comprising a therapy control, coupled to the control system, and adapted to provide one or more therapies based on a result from the arrhythmia discriminator module.

17. A non-transitory machine-readable storage medium comprising instructions, which when executed by a machine, cause the machine to:
- sense one or more sequences of atrial and ventricular contractions associated with the tachyarrhythmia;
- select one or more patterns that represent an onset pattern, the patterns including respective sequences of atrial and ventricular contractions; and
- obtain a first classification of the tachyarrhythmia based on whether a match exists between the one or more sequences of atrial and ventricular contractions and the one or more patterns.

18. The non-transitory machine-readable storage medium of claim 17, comprising instructions, which when executed by the machine, cause the machine to:
- identify a sequence of atrial and ventricular contractions associated with the tachyarrhythmia; and
- classify the sequence as more likely indicative of ventricular tachycardia if two or more ventricular contractions occur between consecutive atrial contractions within the sequence.

19. The non-transitory machine-readable storage medium of claim 17, comprising instructions, which when executed by the machine, cause the machine to:
- identifying a sequence of atrial and ventricular contractions associated with the tachyarrhythmia; and
- classifying the sequence as more likely indicative of supraventricular tachyarrhythmia if two or more atrial contractions occur between consecutive ventricular contractions within the sequence.

20. The non-transitory machine-readable storage medium of claim 17, wherein the one or more patterns define respective sequences of individual atrial and ventricular contractions.

21. The non-transitory machine-readable storage medium of claim 17, wherein the one or more patterns define individual contraction ordering of respective sequences of one or more individual atrial contractions interspersed together with one or more individual ventricular contractions.

22. The non-transitory machine-readable storage medium of claim 17, wherein the one or more patterns are pre-defined.

23. The non-transitory machine-readable storage medium of claim 17, wherein the one or more patterns represent an onset pattern and are selected from the group of: A1-V1-V2-A2, A1-V1-A2-V2, and A1-A2-V1-A3-V2; and wherein the instructions to obtain the first classification include instructions to determine at least one pattern selected from the group appears in the one or more sequences of atrial and ventricular contractions.

* * * * *

UNITED STATES PATENT AND TRADEMARK OFFICE
CERTIFICATE OF CORRECTION

| | | |
|---|---|---|
| PATENT NO. | : 8,145,301 B2 | Page 1 of 1 |
| APPLICATION NO. | : 12/895151 | |
| DATED | : March 27, 2012 | |
| INVENTOR(S) | : Jaeho Kim et al. | |

It is certified that error appears in the above-identified patent and that said Letters Patent is hereby corrected as shown below:

On page 3, under item 56 References Cited, "Other Publications," in column 1, line 20, delete "Aciton" and insert -- Action --, therefor.

In column 28, line 15, in Claim 2, delete "in" and insert -- of --, therefor.

Signed and Sealed this
Nineteenth Day of June, 2012

David J. Kappos
*Director of the United States Patent and Trademark Office*